United States Patent [19]

Greisen et al.

[11] Patent Number: 5,620,847
[45] Date of Patent: Apr. 15, 1997

[54] METHODS AND REAGENTS FOR DETECTION OF BACTERIA IN CEREBROSPINAL FLUID

[75] Inventors: Kay S. Greisen, Oakland; Diane U. Leong, Berkeley, both of Calif.

[73] Assignee: Hoffman-La Roche Inc., Nutley, N.J.

[21] Appl. No.: 244,269

[22] PCT Filed: Jul. 31, 1992

[86] PCT No.: PCT/US92/06365

§ 371 Date: May 16, 1994

§ 102(e) Date: May 16, 1994

[87] PCT Pub. No.: WO93/03186

PCT Pub. Date: Feb. 18, 1993

Related U.S. Application Data

[63] Continuation-in-part of Ser. No. 738,393, Jul. 31, 1991, abandoned, which is a continuation-in-part of Ser. No. 593,176, Oct. 5, 1990, abandoned, and Ser. No. 696,448, May 6, 1991, abandoned.

[51] Int. Cl.$^6$ .............. C12Q 1/68; C12P 19/34; C07H 21/04
[52] U.S. Cl. .............. 435/6; 435/91.2; 536/24.3; 536/24.32
[58] Field of Search ............ 435/91.2, 6; 536/24.3, 536/24.32

[56] References Cited

U.S. PATENT DOCUMENTS

| | | | |
|---|---|---|---|
| 414,542 | 9/1889 | Longiaru et al. | 435/6 |
| 4,683,195 | 7/1987 | Mullis et al. | 435/91.2 |
| 4,683,202 | 7/1987 | Mullis | 435/91.2 |
| 4,717,653 | 1/1988 | Webster | 435/5 |
| 4,800,159 | 1/1989 | Mullis et al. | 435/91.2 |
| 4,820,630 | 4/1989 | Taub | 435/5 |
| 4,851,330 | 7/1989 | Kohne | 435/6 |
| 4,977,251 | 12/1990 | Salyers et al. | 536/24.32 |
| 5,084,565 | 1/1992 | Parodos et al. | 435/6 |

FOREIGN PATENT DOCUMENTS

| | | |
|---|---|---|
| 49025/90 | 8/1990 | Australia. |
| 69475/91 | 7/1991 | Australia. |
| 88/03957 | 6/1988 | WIPO. |
| 90/08841 | 8/1990 | WIPO. |
| WO90/11370 | 10/1990 | WIPO. |
| 91/08305 | 6/1991 | WIPO. |

OTHER PUBLICATIONS

Kristiansen et al., The Lancet, 337:1568–1569 (1991).
Neefs et al., Nuc. Acids Res., 18:2237–2317 (1990).
Weisburg et al., J. Bacteriol., 164:230–236 (1985).
Carbon et al., FEBS Letters, 94:152–156 (1978).
Wilson et al., J. Clin. Micro., 28:1942–1946 (Sep. 1990).
Bottger, E.C., FEMS Micro. Ltrs., 65:171–176 (1989).
Woese, et al, Science, 229:762–765 (1985).
Tsuru et al., Chem. Abst., 110:111361c (1989).
Stackebrandt et al., Intl. J. System. Bacteriology, 38:354–357.
Pramanik et al., Arch. Biochem. & Biophysics, 235:276–282 (1984).
Tsuru et al., Med. Immunology, 16:827–833 (1988).
Lane et al., PNAS, 82:6955–6959 (1985).
White et al., in PCR Protocols: A Guide to Methods and Applications, 315–322 (1990).
Medlin et al., Gene, 71:491–499 (1988).
Atlas and Bej, in PCR Protocols: A Guide to Methods and Applications, 399–406 (1990).
Olive, Michael D., Clin. Micro. 27:261–265 (1989).
Wood et al., PNAS, 82:1585–1588 (1985).
Woese, Carl R., Micro. Reviews, 51:221–271 (1987).
Bryan, Charles S., Clin. Micro. Reviews, 2:329–353 (1989).
Kocher and White, Chap. 13 of PCR Technology: Principles and Applications for DNA Amplification, pp. 137–147 (1989).
Barry et al., Biotechnology, 8:233–236 (1990).
Kocher et al., PNAS, 86:6196–6200 (1989).
Kuritza et al., Abstracts of the General Mtg.—1991 (ASM), p. 84 (D-36) (May 1991).
Collins et al., Intl. J. System. Bacteriology, 41:240–246 (Apr. 1991).
Deneer et al., Applied and Environ. Micro., 57:606–609 (Feb. 1991).
Kristiansen et al., Lancet, 337:1568–1569 (Jun. 1991).
Joklik et al, Zinsser Microbiology, 18th ed. (1984) pp. 444, 459, 485, 689.
Lundeberg et al, (May 1990), "Rapid colorimetric detection of in vitro amplified DNA sequences", 9(4):287–292.
Stratagene catalog (1988), p. 39.
Wilson et al, (1989), "Probe directed at a segment of *Rickettsia rickettsii* rRNA amplified with polymerase chain reaction", J. Clin. Microbiol. 27(12):2692–2696.
Chen et al, (1989), "Broad range DNA probes for detecting and amplifying eubacterial nucleic acids", FEMS Microbiol. Lett. 57:19–24.
Hay et al, (Mar. 1990) "Use of the polymerase chain reaction to detect DNA sequences specific to pathogenic treponemes in cerebrospinal fluid", FEMS Microbiol. Lett. 68:233–238.

*Primary Examiner*—Stephanie W. Zitomer
*Assistant Examiner*—Jeffrey Fredman
*Attorney, Agent, or Firm*—George W. Johnston; Patricia S. Rocha-Tramaloni; Raina Seminow

[57] ABSTRACT

Methods and reagents are provided for detecting bacterial nucleic acids in cerebrospinal fluid. In a preferred embodiment, a panel of probes is provided for detecting and identifying causal agents of meningitis.

4 Claims, 21 Drawing Sheets

NEISSERIA MENINGITIDIS
SEQ ID No. 28

| | | | | | |
|---|---|---|---|---|---|
| 1 | GTCATTAGTT | GCCATCATTC | AGTTGGGCAC | TCTAATGAGA | CTGCCGGTGA |
| 51 | CAAGCCGGAG | GAAGGTGGGG | ATGACGTCAA | GTCCTCATGG | CCCTTATGAC |
| 101 | CAGGGCTTCA | CACGTCATAC | AATGGTCGGT | ACAGAGGGTA | GCCAAGCCGC |
| 151 | GAGGCGGAGC | CAATCTCACA | AAACCGATCG | TAGTCCGGAT | TGCACTCTGC |
| 201 | AACTCGAGTG | CATGAAGTCG | GAATCGCTAG | TAATCGCAGG | TCAGCATACT |
| 251 | GCGGTGAATA | CGTTCCCGGG | TCTTGTACAC | ACCGCCCGTC | ACACCATGGG |
| 301 | AGTGGGGGAT | ACCAGAAGTA | GGTAGGGTAA | CCGCAAGGAG | CCCGCTTACC |
| 351 | ACGGTATGCT | TCATGACTGG | GGTGA | | |

FIG. 1A

STREPTOCOCCUS AGALACTIAE
SEQ ID No. 29

| | | | | | |
|---|---|---|---|---|---|
| 1 | TTGCCATCAT | TAAGTTGGGC | ACTCTAGCGA | GACTGCCGGT | AATAAACCGG |
| 51 | AGGAAGGTGG | GGATGACGTC | AAATCATCAT | GCCCCTTATG | ACCTGGGCTA |
| 101 | CACACGTGCT | ACAATGGTTG | GTACAACGAG | TCGCAAGCCG | GTGACGGCAA |
| 151 | GCTAATCTCT | TAAAGCCAAT | CTCAGTTCGG | ATTGTAGGCT | GCAACTCGCC |
| 201 | TACATGAAGT | CGGAATCGCT | AGTAATCGCG | GATCAGCACG | CCGCGGTGAA |
| 251 | TACGTTCCCG | GGCCTTGTAC | ACCGCCCG | TCACACCACG | AGAGTTTGTA |
| 301 | ACACCCGAAG | TCGGTGAGGT | AACCTTTTAG | GAGCCAGCCG | CCTAAGGTGG |
| 351 | GATAGATGAT | TGGGGTGACG | TCGTAACAAG | GTAGCC | |

FIG. 1B

STREPTOCOCCUS PNEUMONIAE
SEQ ID No. 30

| | | | | | |
|---|---|---|---|---|---|
| 1 | AGTTGCCATC | ATTTAGTTGG | GCACTCTAGC | GAGACTGCCG | GTAATAAACC |
| 51 | GGAGGAAGGT | GGGGATGACG | TCAAATCATC | ATGCCCCTTA | TGACCTGGGC |
| 101 | TACACACGTG | CTACAATGGC | TGGTACAACG | AGTCGCAAGC | CGGTGACGGC |
| 151 | AAGCTAATCT | CTTAAAGCCA | GTCTCAGTTC | GGATTGTAGG | CTGCAACTCG |
| 201 | CCTACATGAA | GTCGGAATCG | CTAGTAATCG | CGGATCAGCA | CGCCGCGGTG |
| 251 | AATACGTTCC | CGGGCCTTGT | ACACACCGCC | CGTCACACCA | CGAGAGTTTG |
| 301 | TAACACCCGA | AGTCGGTGAG | GTAACCGTAA | GGAGCCAGCC | GCCTAAGGTG |
| 351 | GGATAGATGA | TTGGGGTGAA | GTCGTAACAA | GGTAGC | |

FIG. 1C

STAPHYLOCOCCUS EPIDERMIDIS
SEQ ID No. 31

```
  1  CTTAAGCTTA  GTTGCCATCA  TTAAGTTGGG  CACTCTAAGT  TGACGCCGGT
 51  GACAAACCGG  AGGAAGGTGG  GGATGACGTC  AAATCATCAT  GCCCCTTATG
101  ATTTGGGCTA  CACACGTGCT  ACAATGGACA  ATACAAAGGG  YAGCGAAACC
151  GCGAGGTCAA  GCAAATCCCA  TAAAGTTGTT  CTCAGTTCGG  ATTGTAGTCT
201  GCAACTCGAC  TATATGAAGC  TGGAATCGCT  AGTAATCGTA  GATCAGCATG
251  CTACGGTGAA  TACGTTCCCG  GGTCTTGTAC  ACACCGCCCG  TCACACCACG
301  AGAGTTTGTA  ACACCCGAAG  CCGGTGGAGT  AACCATTTGG  AGCTAGCGTC
351  GAAGGTGGGA  CAAATGATTG  GGGTGAGTCG  TAACAAGGTA  GCCG
```

FIG. 1D

STAPHYLOCOCCUS AUREUS
SEQ ID No. 47

```
  1  GGGCACTCTA  AGTTGACNGC  CGGTGACAAA  CCGGAGGAAG  GTGGGGATGA
 51  CGTCAAATCA  TCATGCCCCT  TATGATTTGG  GCTACACACG  TGCTACAATG
101  GACAATACAA  AGGGCAGCGA  AACCGCGAGG  TCAAGCAAAT  CCCATAAAGT
151  TGTTCTCAGT  TCGGATTGTA  GTCTGCAACT  CGACTACATG  AAGCTGGAAT
201  CGCTAGTAAT  CGTAGATCAG  CATGCTACGG  TGAATACGTT  CCCGGGTCTT
251  GTACACACCG  CCCGTCACAC  CACGAGAGTT  TGTAACACCC  GAAGCCGGTG
301  GAGTAACCTT  TTAGGAGCTA  GCNGTCGAAG  GTGGGACAAA  TGATTGGGGT
351  GAGTCGTAAC  AAGGTA
```

FIG. 1E

STREPTOCOCCUS PYOGENES
SEQ ID No. 48

```
  1  AGTTGCCATC  ATTAAGTTGG  GCACTCTAGC  GAGACTGCCG  GTAATAAACC
 51  GGAGGAAGGT  GGGGATGACG  TCAAATCATC  ATGCCCCTTA  TGACCTGGGC
101  TACACACGTG  CTACAATGGT  TGGTACAACG  AGTCGCAAGC  CGGTGACGGC
151  AAGCTAATCT  CTTAAAGCCA  ATCTCAGTTC  GGATTGTAGG  CTGCAACTCG
201  CCTACATGAA  GTCGGAATCG  CTAGTAATCG  CGGATCAGCA  CGCCGCGGTG
251  AATACGTTCC  CGGGCCTTGT  ACACACCGCC  CGTCACACCA  CGAGAGTTTG
301  TAACACCCGA  GTCGGTGAGG  TAACCTATTA  GGAGCCGCCG  CCTAAGGTGG
351  GATAGATGAT  TGGGGTGAGT  CGTAACAAGG  TAGCCG
```

FIG. 1F

| SPECIES NAME | FORMAT | SEQUENCE I.D. NUMBER | PROBE | POSITION | SEQUENCE |
|---|---|---|---|---|---|
| Bacillus species | I | 1 | RDR502 | 1354-1378 (−) | GTATTCACCGCGGGCATGCTGATCCG |
| Bacillus species | I, II | 2 | COR48 | 1357-1377 (−) | TATTCACCGCGGCATGCTGAT |
| coagulase-negative Staphylococci | I, II | 3 | COR02 | 1443-1465 (+) | AGTAACCATTGGAGCTAGCCGT |
| coagulase-negative Staphylococci | I | 4 | RDR512 | 1440-1464 (−) | CGGCTAGCTCCAAAAGGTTACTCTA |
| coagulase-negative Staphylococci | I, II | 5 | COR05 | 1440-1464 (−) | CGGCTAGCTCTAAAAGGTTACTCTA |
| coagulase-negative Staphylococci | I | 6 | RDR325 | 1443-1467 (−) | CGACGGCTAGCTCCAAATGGTTACT |
| Corynebacterium species | I, II | 7 | COR36 | 1228-1252 (+) | CACATGCTACAAGGGTCGGTACAGT |
| Corynebacterium species | I | 8 | RDR510 | 1228-1252 (−) | ACTGTACCGACCACTTGTAGCATGTG |
| Escherichia coli | I, II | 9 | RDR140 | 1458-1482 (+) | GGCGCTTACCACTTTGTGATTCATG |
| Haemophilus influenzae | I, II | 10 | RDR125 | 1416-1440 (+) | GGAGTGGGTTGTACCAGAAGTAGAT |
| Listeria monocytogenes | I, II | 11 | RDR230 | 1277-1301 (+) | CTAATCCCATAAAACTATTCTCAGT |
| Mycobacterium species | I, II | 12 | COR38 | 1244-1266 (+) | CGGTACAAAGGGCTGCGATGCG |
| Neisseria meningitidis | I | 13 | RDR307 | 1450-1474 (+) | GCAAGGAGCCCGCTTACCACGGTAT |
| Neisseria meningitidis | I, II | 14 | COR28 | 1261-1283 (+) | AAGCCGGAGGCGGAGCCAATCT |
| Propionibacterium acnes | I, II | 15 | RDR328 | 1274-1298 (−) | GAGACCGGCTTTCCGAGATTCGCTC |
| Propionibacterium species | I, II | 16 | COR44 | 1402-1423 (−) | CCAACTTTCATGACTTGACGGG |
| Propionibacterium species | I | 17 | RDR514 | 1376-1400 (+) | GGTGTGTACAAGCCCGGGAACGTA |
| Staphylococcus aureus | I | 18 | RDR327 | 1435-1458 (+) | GCCGGTGGAGTGAGTAACCTTTAGGAGC |
| Staphylococcus aureus | I, II | 19 | COR26 | 1436-1456 (+) | CCGGTGGAGTAACCTTTAGGA |
| Streptococcus agalactiae | I | 20 | RDR306 | 1237-1261 (−) | TTGCGACTCGTTGTACCAACCATTG |
| Streptococcus agalactiae | I, II | 21 | VP109 | 1278-1302 (−) | AACTGAGATTGGCTTTAAGAGATTA |
| Streptococcus agalactiae | I | 22 | KG0001 | 1278-1302 (+) | TAATCTCTTAAAGCCAATCTCAGTT |
| Streptococcus pneumoniae | I | 23 | RDR224 | 1281-1305 (−) | CCGAACTGAGACTGGCTTTAAGAGA |
| Streptococcus pneumoniae | I | 24 | RDR462 | 1278-1302 (−) | AACTGAGACTGGCTTTAAGAGATTA |
| Streptococcus pneumoniae | I, II | 25 | VP111 | 1280-1302 (−) | AACTGAGACTGGCTTTAAGAGAT |

FIG. 2

| STRAIN | REFERENCE | PROBE RDR306 S. agalactiae | PROBE RDR230 L. monocytogenes | PROBE RDR224 S. pneumoniae | PROBE RDR125 H. influenzae | PROBE RDR307 N. meningitidis | PROBE RDR140 E. coli |
|---|---|---|---|---|---|---|---|
| *Neisseria meningitidis* | | | | | | | |
| serotype A | CMCC 2801 | - | - | - | - | + | - |
| serotype A | ATCC 13077 | - | - | - | - | + | - |
| serotype A | CDC | N.D. | N.D. | N.D. | N.D. | + | N.D. |
| serotype B | CDC | N.D. | N.D. | N.D. | N.D. | - | N.D. |
| serotype C | CDC | N.D. | N.D. | N.D. | N.D. | - | N.D. |
| serotype Y | CDC | N.D. | N.D. | N.D. | N.D. | - | N.D. |
| serotype W135 | CDC | N.D. | N.D. | N.D. | N.D. | - | N.D. |
| *Haemophilus influenzae* | ATCC 33391 | - | - | - | + | - | - |
| | 2423 | - | - | - | + | - | - |
| | 503-1156 | - | - | - | + | - | - |
| | 503-1148 | - | - | - | + | - | - |
| | 503-1155 | - | - | - | + | - | - |
| | 503-1154 | - | - | - | + | - | - |
| *Streptococcus pneumoniae* | ATCC 33400 | - | - | + | - | - | - |
| | ATCC 6303 | - | - | + | - | - | - |
| | 4366 | - | - | + | - | - | - |
| | 4471 | - | - | + | - | - | - |
| *Escherichia coli* | Strain B | - | - | - | - | - | + |
| | ATCC 11775 | - | - | - | - | - | + |
| | 9 | - | - | - | - | - | + |
| | P3478 | - | - | - | - | - | + |
| | 2889 | - | - | - | - | - | + |
| | 340 | - | - | - | - | - | + |
| *Streptococcus agalactiae* | ATCC 13813 | + | - | - | - | - | - |
| | 4352 | + | - | - | - | - | - |
| | 4353 | + | - | - | - | - | - |
| | 4354 | + | - | - | - | - | - |
| | 4355 | + | - | - | - | - | - |

FIG. 3A

| STRAIN | REFERENCE | PROBE RDR306 S. agalactiae | PROBE RDR230 L. monocytogenes | PROBE RDR224 S. pneumoniae | PROBE RDR125 H. influenzae | PROBE RDR307 N. meningitidis | PROBE RDR140 E. coli |
|---|---|---|---|---|---|---|---|
| | 4356 | + | - | - | - | | - |
| Listeria monocytogenes | | | | | | | |
| serotype 1/2a | ATCC 15313 | - | + | - | - | - | - |
| serotype 1/2c | G0282 | - | + | - | - | - | - |
| serotype 1/2c | G0288 | - | + | - | - | - | - |
| serotype 4b | F9784 | - | + | - | - | - | - |
| serotype 4b | G0278 | - | + | - | - | - | - |
| serotype 3b | F9841 | - | - | - | - | - | - |
| Neisseria gonorrhoeae | CMCC 2783 | - | - | - | - | - | - |
| | ATCC 19424 | - | - | - | - | - | - |
| | 31917 | - | - | - | - | - | - |
| | 31959 | - | - | - | - | - | - |
| | 32171 | - | - | - | - | - | - |
| | 32213 | - | - | - | - | - | - |
| N. sicca | Rush isolate | N.D. | N.D. | N.D. | N.D. | + | N.D. |
| N. polysaccharea | ATCC 43768 | N.D. | N.D. | N.D. | N.D. | - | N.D. |
| Eikenella corrodens | ATCC 23834 | N.D. | N.D. | N.D. | N.D. | - | N.D. |
| Corynebacterium genitalium | ATCC 33030 | - | - | - | - | - | - |
| Corynebacterium pseudotuberculosis | ATCC 19410 | - | - | - | - | - | - |
| Corynebacterium xerosis | ATCC 373 | - | - | - | - | - | - |
| Staphylococcus epidermidis | ATCC 12228 | - | - | - | - | - | - |
| | ATCC 14990 | - | - | - | - | - | - |
| | 4233 | - | - | - | - | - | - |
| | 4234 | - | - | - | - | - | - |
| | 4235 | - | - | - | - | - | - |
| | 4236 | - | - | - | - | - | - |
| Staphylococcus aureus | ATCC 33589 | - | - | - | - | - | - |
| | ATCC 25923 | - | - | - | - | - | - |
| | 4241 | - | - | - | - | - | - |

FIG. 3B

| STRAIN | REFERENCE | PROBE RDR306 S. agalactiae | PROBE RDR230 L. monocytogenes | PROBE RDR224 S. pneumoniae | PROBE RDR125 H. influenzae | PROBE RDR307 N. meningitidis | PROBE RDR140 E. coli |
|---|---|---|---|---|---|---|---|
| | 4247 | - | - | - | | - | - |
| | 4248 | - | - | - | | - | - |
| | 4249 | | | - | - | | |
| S. auricularis | ATCC 33753 | N.D. | N.D. | N.D. | N.D. | N.D. | N.D. |
| S. saccarolyticus | ATCC 14953 | N.D. | N.D. | N.D. | N.D. | - | N.D. |
| S. capitis capitis | ATCC 35661 | N.D. | N.D. | N.D. | N.D. | N.D. | N.D. |
| S. cohnii cohnii | ATCC 35662 | N.D. | N.D. | N.D. | N.D. | N.D. | N.D. |
| S. haemolyticus | ATCC 29970 | N.D. | N.D. | N.D. | N.D. | N.D. | N.D. |
| S. hominis | ATCC 29885 | N.D. | N.D. | N.D. | N.D. | N.D. | N.D. |
| S. saprophyticus | ATCC 15305 | N.D. | N.D. | N.D. | N.D. | N.D. | N.D. |
| S. warneri | ATCC 27836 | N.D. | N.D. | N.D. | N.D. | N.D. | N.D. |
| Streptococcus salivarius | ATCC 13419 | - | - | - | - | - | - |
| S. equi | ATCC 7073 | - | N.D. | - | N.D. | N.D. | N.D. |
| S. group G | NCTC 9682 | + | N.D. | - | N.D. | N.D. | N.D. |
| S. pyogenes | 4286 | + | N.D. | - | N.D. | N.D. | N.D. |
| S. dysgalactiae | ATCC 19615 | + | N.D. | - | N.D. | N.D. | N.D. |
| S. anginosus | ATCC 43078 | + | N.D. | - | N.D. | N.D. | N.D. |
| S. constellatus | ATCC 12395 | - | N.D. | +/- | N.D. | N.D. | N.D. |
| S. milleri | ATCC 27823 | - | N.D. | - | N.D. | N.D. | N.D. |
| S. mitis | 4224 | - | N.D. | +/- | N.D. | N.D. | N.D. |
| S. mutans | NCTC 3165 | - | N.D. | + | N.D. | N.D. | N.D. |
| S. sanguis | ATCC 25175 | - | N.D. | - | N.D. | N.D. | N.D. |
| S. intermedius | ATCC 10556 | - | N.D. | +/- | N.D. | N.D. | N.D. |
| Bacillus subtilis | ATCC 27335 | - | N.D. | +/- | N.D. | N.D. | N.D. |
| | BD224 | - | - | - | - | - | - |
| | 6051 | - | - | - | - | - | - |
| | 558 | - | | - | | - | - |
| B. cereus | 11778 | - | - | - | | - | - |

FIG. 3C

| STRAIN | | PROBE RDR306 S. agalactiae | PROBE RDR230 L. monocytogenes | PROBE RDR224 S. pneumoniae | PROBE RDR125 H. influenzae | PROBE RDR307 N. meningitidis | PROBE RDR140 E. coli |
|---|---|---|---|---|---|---|---|
| | REFERENCE | | | | | | |
| | H | - | | - | - | - | - |
| B. amyloliquefaciens | ATCC 72 | | N.D. | - | N.D. | - | N.D. |
| B. pumilis | ATCC 8186 | - | N.D. | - | N.D. | N.D. | N.D. |
| B. brevis | ATCC 8246 | - | N.D. | - | N.D. | N.D. | N.D. |
| Propionibacterium acnes | ATCC 6919 | - | - | - | - | - | - |
| P. avidum | ATCC 25577 | N.D. | N.D. | N.D. | N.D. | - | N.D. |
| P. granulosum | ATCC 25564 | N.D. | N.D. | N.D. | N.D. | - | N.D. |
| P. lymphophilum | ATCC 27520 | N.D. | N.D. | N.D. | N.D. | N.D. | N.D. |
| Flavobacterium meningosepticum | ATCC 13253 | - | - | - | - | - | - |

FIG. 3D

| STRAIN | REFERENCE | PROBE RDR328 P.acnes | PROBE RDR325 coag.neg. Staph | PROBE RDR462 S. pneumoniae | PROBE KG0001 S. agalactiae | PROBE COR28 N. meningitidis | PROBE RDR502 Bacillus spp. |
|---|---|---|---|---|---|---|---|
| *Neisseria meningitidis* | | | | | | | |
| serotype A | CMCC 2801 | - | - | - | - | + | - |
| serotype A | ATCC 13077 | - | - | - | - | + | - |
| serotype A | CDC | N.D. | N.D. | N.D. | N.D. | + | - |
| serotype B | CDC | N.D. | N.D. | N.D. | N.D. | + | - |
| serotype C | CDC | N.D. | N.D. | N.D. | N.D. | + | - |
| serotype Y | CDC | N.D. | N.D. | N.D. | N.D. | + | - |
| serotype W135 | CDC | N.D. | N.D. | N.D. | N.D. | + | - |
| *Haemophilus influenzae* | ATCC 33391 | - | - | - | - | - | - |
| | 2423 | - | - | - | - | - | - |
| | 503-1156 | - | - | - | - | - | - |
| | 503-1148 | - | - | - | - | - | - |
| | 503-1155 | - | - | - | - | - | - |
| | 503-1154 | - | - | - | - | - | - |
| *Streptococcus pneumoniae* | ATCC 33400 | - | - | + | - | - | - |
| | ATCC 6303 | - | - | + | - | - | - |
| | 4366 | - | - | + | - | - | - |
| | 4471 | - | - | + | - | - | - |
| *Escherichia coli* | Strain B | - | - | - | - | - | - |
| | ATCC 11775 | - | - | - | - | - | - |
| | 9 | - | - | - | - | - | - |
| | P3478 | - | - | - | - | - | - |
| | 2889 | - | - | - | - | - | - |
| | 340 | - | - | - | - | - | - |
| *Streptococcus agalactiae* | ATCC 13813 | - | - | - | + | - | - |
| | 4352 | - | - | - | + | - | - |
| | 4353 | - | - | - | + | - | - |
| | 4354 | - | - | - | + | - | - |
| | 4355 | - | - | - | + | - | - |

FIG. 3E

| STRAIN | REFERENCE | PROBE RDR328 P.acnes | PROBE RDR325 coag.neg. Staph | PROBE RDR462 S. pneumoniae | PROBE KG0001 S. agalactiae | PROBE COR28 N. meningitidis | PROBE RDR502 Bacillus spp. |
|---|---|---|---|---|---|---|---|
| | 4356 | - | | | + | N.D. | - |
| Listeria monocytogenes | ATCC 15313 | - | - | - | - | - | - |
| | G0282 | - | - | - | - | - | - |
| | G0288 | - | - | - | - | - | - |
| | F9784 | - | - | - | - | - | - |
| | G0278 | - | - | - | - | - | - |
| | F9841 | - | - | - | - | - | - |
| Neisseria gonorrhoeae | CMCC 2783 | - | - | - | - | + | - |
| | ATCC 19424 | - | - | - | - | + | - |
| | 31917 | - | - | - | - | + | - |
| | 31959 | - | - | - | - | + | - |
| | 32171 | - | - | - | - | + | - |
| | 32213 | - | - | - | - | - | - |
| N. sicca | Rush isolate | - | - | N.D. | N.D. | - | - |
| N. polysaccharea | ATCC43768 | N.D. | - | N.D. | N.D. | - | - |
| Eikenella corrodens | ATCC 23834 | - | - | N.D. | N.D. | - | - |
| Corynebacterium genitalium | ATCC 33030 | - | - | - | - | - | - |
| Corynebacterium pseudotuberculosis | ATCC 19410 | - | - | - | - | - | - |
| Corynebacterium xerosis | ATCC 373 | - | - | - | - | - | - |
| Staphylococcus epidermidis | ATCC 12228 | - | + | - | - | - | - |
| | ATCC 14990 | - | + | - | - | - | - |
| | 4233 | - | + | - | + | - | - |
| | 4234 | - | + | - | - | - | - |
| | 4235 | - | + | - | - | - | - |
| | 4236 | - | - | - | - | - | - |
| Staphylococcus aureus | ATCC 33589 | - | - | - | - | - | - |
| | ATCC 25923 | - | - | - | - | - | - |
| | 4241 | - | - | - | - | - | - |

FIG. 3F

| STRAIN | REFERENCE | PROBE RDR328 P.acnes | PROBE RDR325 coag.neg. Staph | PROBE RDR462 S. pneumoniae | PROBE KG0001 S. agalactiae | PROBE COR28 N. meningitidis | PROBE RDR502 Bacillus spp. |
|---|---|---|---|---|---|---|---|
|  | 4247 | - | - | - | - | - | - |
|  | 4248 | - | - | - | - | - | - |
|  | 4249 | - | - | - | - | - | - |
| S. auricularis | ATCC 33753 | N.D. | - | N.D. | N.D. | N.D. | - |
| S. saccarolyticus | ATCC 14953 | N.D. | - | N.D. | N.D. | N.D. | - |
| S. capitis capitis | ATCC 35661 | N.D. | - | N.D. | N.D. | N.D. | N.D. |
| S. cohnii cohnii | ATCC 35662 | N.D. | - | N.D. | N.D. | N.D. | N.D. |
| S. haemolyticus | ATCC 29970 | N.D. | + | N.D. | N.D. | N.D. | N.D. |
| S. hominis | ATCC 29885 | N.D. | - | N.D. | N.D. | N.D. | N.D. |
| S. saprophyticus | ATCC 15305 | N.D. | - | N.D. | N.D. | N.D. | N.D. |
| S. warneri | ATCC 27836 | N.D. | - | N.D. | N.D. | N.D. | N.D. |
| Streptococcus salivarius | ATCC 13419 | - | - | - | + | - | - |
| S. equi | ATCC 7073 | N.D. | - | - | + | N.D. | - |
| S. group G | NCTC 9682 | N.D. | - | - | - | N.D. | - |
| S. pyogenes | 4286 | N.D. | N.D. | - | + | N.D. | - |
| S. dysgalactiae | ATCC 19615 | N.D. | N.D. | - | + | N.D. | - |
| S. anginosus | ATCC 43078 | N.D. | N.D. | - | + | N.D. | - |
| S. constellatus | ATCC 12395 | N.D. | N.D. | - | - | N.D. | - |
| S. milleri | ATCC 27823 | N.D. | N.D. | - | - | N.D. | - |
| S. mitis | 4224 | N.D. | N.D. | + | - | N.D. | - |
| S. mutans | NCTC 3165 | N.D. | N.D. | - | - | N.D. | - |
| S. sanguis | ATCC 25175 | N.D. | N.D. | - | - | N.D. | - |
| S. intermedius | ATCC 10556 | N.D. | N.D. | - | - | N.D. | - |
|  | ATCC 27335 | N.D. | N.D. | - | - | N.D. | - |
| Bacillus subtilis | BD224 | - | - | - | - | - | + |
|  | 6051 | - | - | - | - | - | + |
|  | 558 | - | - | - | - | - | + |
| B. cereus | 11778 | - | - | - | - | - | + |

FIG. 3G

| STRAIN | REFERENCE | PROBE RDR328 P.acnes | PROBE RDR325 coag.neg. Staph | PROBE RDR462 S. pneumoniae | PROBE KG0001 S. agalactiae | PROBE COR28 N. meningitidis | PROBE RDR502 Bacillus spp. |
|---|---|---|---|---|---|---|---|
| B. amyloliquefaciens | H | - | - | - | - | - | + |
| B. pumilis | ATCC 72 | N.D. | N.D. | - | - | N.D. | + |
| B. brevis | ATCC 8186 | N.D. | N.D. | - | - | N.D. | + |
|  | ATCC 8246 | N.D. | N.D. | - | - | N.D. | + |
| Propionibacterium acnes | ATCC 6919 | + | - | - | - | - | - |
| P. avidum | ATCC 25577 | + | - | N.D. | N.D. | N.D. | N.D. |
| P. granulosum | ATCC 25564 | - | - | N.D. | N.D. | N.D. | N.D. |
| P. lymphophilum | ATCC 27520 | - | N.D. | N.D. | N.D. | N.D. | N.D. |
| Flavobacterium meningosepticum | ATCC 13253 | - | - | - | - | - | - |

FIG. 3H

| STRAIN | | PROBE RDR510 Corynebac. spp. | PROBE RDR514 Propionibac. spp. | PROBE RDR512 coag.neg. Staph | PROBE RDR327 S. aureus |
|---|---|---|---|---|---|
| | REFERENCE | | | | |
| Neisseria meningitidis | CMCC 2801 | | | | |
| serotype A | ATCC 13077 | - | - | - | - |
| serotype A | CDC | - | - | - | - |
| serotype B | CDC | - | - | - | - |
| serotype C | CDC | - | - | - | - |
| serotype Y | CDC | - | - | - | - |
| serotype W135 | CDC | - | - | - | - |
| Haemophilus influenzae | ATCC 33391 | - | - | - | - |
| | 2423 | - | - | - | - |
| | 503-1156 | - | - | - | - |
| | 503-1148 | - | - | - | - |
| | 503-1155 | - | - | - | - |
| | 503-1154 | - | - | - | - |
| Streptococcus pneumoniae | ATCC 33400 | - | - | - | - |
| | ATCC 6303 | - | - | - | - |
| | 4366 | - | - | - | - |
| | 4471 | - | - | - | - |
| Escherichia coli | Strain B | - | - | - | - |
| | ATCC 11775 | - | - | - | - |
| | 9 | - | - | - | - |
| | P3478 | - | - | - | - |
| | 2889 | - | - | - | - |
| | 340 | - | - | - | - |
| Streptococcus agalactiae | ATCC 13813 | - | - | - | - |
| | 4352 | - | - | - | - |
| | 4353 | - | - | - | - |
| | 4354 | - | - | - | - |
| | 4355 | - | - | - | - |

FIG. 3I

| STRAIN | REFERENCE | PROBE RDR510 Corynebac. spp. | PROBE RDR514 Propionibac. spp. | PROBE RDR512 coag.neg. Staph | PROBE RDR327 S. aureus |
|---|---|---|---|---|---|
| | 4356 | - | | | - |
| Listeria monocytogenes | ATCC 15313 | - | - | - | - |
| | G0282 | - | - | - | - |
| | G0288 | - | - | - | - |
| | F9784 | - | - | - | - |
| | G0278 | - | - | - | - |
| | F9841 | - | - | - | - |
| Neisseria gonorrhoeae | CMCC 2783 | - | - | - | - |
| | ATCC 19424 | - | - | - | - |
| | 31917 | - | - | - | - |
| | 31959 | - | - | - | - |
| | 32171 | - | - | - | - |
| | 32213 | - | - | - | - |
| N. sicca | Rush isolate | - | - | - | - |
| N. polysaccharea | ATCC43768 | - | - | - | - |
| Eikenella corrodens | ATCC 23834 | - | - | - | - |
| Corynebacterium genitalium | ATCC 33030 | + | - | - | - |
| Corynebacterium pseudotuberculosis | ATCC 19410 | + | - | - | - |
| Corynebacterium xerosis | ATCC 373 | - | - | - | - |
| Staphylococcus epidermidis | ATCC 12228 | - | - | - | - |
| | ATCC 14990 | - | - | - | - |
| | 4233 | | | | |
| | 4234 | | | | |
| | 4235 | | | | |
| | 4236 | | | | |
| Staphylococcus aureus | ATCC 33589 | - | - | - | + |
| | ATCC 25923 | - | - | - | + |
| | 4241 | - | - | - | + |

FIG. 3J

| STRAIN | REFERENCE | PROBE RDR510 Corynebac. spp. | PROBE RDR514 Propionibac. spp. | PROBE RDR512 coag.neg. Staph | PROBE RDR327 S. aureus |
|---|---|---|---|---|---|
| | 4247 | - | - | - | + |
| | 4248 | - | - | - | + |
| | 4249 | - | - | - | + |
| S. auricularis | ATCC 33753 | - | - | + | - |
| S. saccarolyticus | ATCC 14953 | - | - | + | - |
| S. capitis capitis | ATCC 35661 | N.D. | N.D. | + | + |
| S. cohnii cohnii | ATCC 35662 | N.D. | N.D. | - | - |
| S. haemolyticus | ATCC 29970 | N.D. | N.D. | - | - |
| S. hominis | ATCC 29885 | N.D. | N.D. | - | - |
| S. saprophyticus | ATCC 15305 | N.D. | N.D. | - | - |
| S. warneri | ATCC 27836 | - | - | - | - |
| Streptococcus salivarius | ATCC 13419 | - | - | - | - |
| S. equi | ATCC 7073 | - | - | - | N.D. |
| S. group G | NCTC 9682 | - | - | - | N.D. |
| S. pyogenes | 4286 | - | - | - | N.D. |
| S. dysgalactiae | ATCC 19615 | - | - | - | N.D. |
| S. anginosus | ATCC 43078 | - | - | - | N.D. |
| S. constellatus | ATCC 12395 | - | - | - | N.D. |
| S. milleri | ATCC 27823 | - | - | - | N.D. |
| S. mitis | 4224 | - | - | - | N.D. |
| S. mutans | NCTC 3165 | - | - | - | N.D. |
| S. sanguis | ATCC 25175 | - | - | - | N.D. |
| S. intermedius | ATCC 10556 | - | - | - | N.D. |
| Bacillus subtilis | ATCC 27335 | - | - | - | N.D. |
| | BD224 | - | - | - | - |
| | 6051 | - | - | - | - |
| | 558 | - | - | - | - |
| B. cereus | 11778 | - | - | - | - |

FIG. 3K

| STRAIN | REFERENCE | PROBE RDR510 Corynebac. spp. | PROBE RDR514 Propionibac. spp. | PROBE RDR512 coag.neg. Staph | PROBE RDR327 S. aureus |
|---|---|---|---|---|---|
| B. amyloliquefaciens | H | - | - | - | - |
| B. pumilis | ATCC 72 | - | - | - | N.D. |
| B. brevis | ATCC 8186 | - | - | - | N.D. |
| | ATCC 8246 | - | - | - | N.D. |
| Propionibacterium acnes | ATCC 6919 | - | + | - | - |
| P. avidum | ATCC 25577 | - | + | - | - |
| P. granulosum | ATCC 25564 | - | + | - | - |
| P. lymphophilum | ATCC 27520 | - | - | - | N.D. |
| Flavobacterium meningosepticum | ATCC 13253 | - | - | - | - |

FIG. 3L

Format II Specificity Testing

| SPECIES | REFERENCE | PROBE RDR245 Universal | PROBE RW03 Gram-Positive | PROBE RDR476 Gram-negative | PROBE RDR477 Gram-negative | PROBE RDR125 H. influenzae |
|---|---|---|---|---|---|---|
| Haemophilus influenzae | Nutley 503-1156 | + | - | + | - | + |
| Streptococcus pneumoniae | ATCC 6303 | + | + | - | - | - |
| Escherichia coli | ATCC 11775 | + | - | + | - | - |
| Listeria monocytogenes | G0282 | + | + | - | - | - |
| S. agalactiae | ATCC 13813 | + | + | - | - | - |
| S. mitis | NCTC 3165 | + | N.D. | N.D. | N.D. | N.D. |
| S. milleri | 4224 | + | N.D. | N.D. | N.D. | N.D. |
| S. equi | NCTC 9682 | + | - | + | + | - |
| Neisseria meningitidis serotype A | ATCC 13077 | + | N.D. | N.D. | N.D. | N.D. |
| serotype A | CDC | + | N.D. | N.D. | N.D. | N.D. |
| serotype B | CDC | + | N.D. | N.D. | N.D. | N.D. |
| serotype C | CDC | + | N.D. | N.D. | N.D. | N.D. |
| serotype Y | CDC | + | N.D. | N.D. | N.D. | N.D. |
| serotype W135 | CDC | + | N.D. | N.D. | N.D. | N.D. |
| N. polysaccharea | ATCC 43768 | + | N.D. | N.D. | N.D. | N.D. |
| N. gonorrhoeae kochii | NRL 32895 | + | N.D. | - | - | - |
| N. cinerea | CDC 10050 | + | + | N.D. | N.D. | N.D. |
| N. sicca | Rush isolate | + | N.D. | N.D. | N.D. | N.D. |
| Eikenella corrodens | ATCC 23834 | + | N.D. | N.D. | N.D. | N.D. |
| Bacillus subtilis | Nutley 558 | + | + | - | - | - |
| Corynebacterium pseudotuberculosis | ATCC 19410 | + | N.D. | - | - | - |
| C. jeikeium | ATCC 43734 | + | N.D. | N.D. | N.D. | N.D. |
| C. genitalium | ATCC 33030 | + | N.D. | N.D. | N.D. | N.D. |
| C. xerosis | ATCC 373 | + | N.D. | N.D. | N.D. | N.D. |
| Propionibacterium acnes | ATCC 6919 | + | + | - | - | - |
| Staphylococcus epidermidis | Basel 4233 | + | + | - | - | - |

FIG. 4A

| Format II Specificity Testing | | PROBE RDR245 | PROBE RW03 | PROBE RDR476 | PROBE RDR477 | PROBE RDR125 |
|---|---|---|---|---|---|---|
| SPECIES | REFERENCE | Universal | Gram-positive | Gram-negative | Gram-negative | H. influenzae |
| S. capitis capitis | ATCC 35661 | + | N.D. | N.D. | N.D. | N.D. |
| S. cohnii | ATCC 35662 | + | N.D. | N.D. | N.D. | N.D. |
| S. haemolyticus | ATCC 29970 | + | N.D. | N.D. | N.D. | N.D. |
| S. saprophyticus | ATCC 15305 | + | N.D. | N.D. | N.D. | N.D. |
| S. warneri | ATCC 27836 | + | N.D. | N.D. | N.D. | N.D. |
| S. auricularis | ATCC 33753 | + | N.D. | N.D. | N.D. | N.D. |
| S. saccharolyticus | ATCC 14953 | + | N.D. | N.D. | N.D. | N.D. |
| S. aureus | Basel 4247 | + | + | − | − | − |
| Mycobacterium tuberculosis | UCSF isolate | + | + | − | − | − |
| Mycobacterium intracellulare | UCSF isolate | + | + | − | − | − |

FIG. 4B

| Format II Specificity Testing | | | | | | | |
|---|---|---|---|---|---|---|---|
| | | PROBE VP111 | PROBE RDR140 | PROBE RDR230 | PROBE VP109 | PROBE COR28 | PROBE COR48 |
| SPECIES | REFERENCE | S.pneumoniae | E.coli/enteric | L.monocytogen. | S.agalactiae | N.meningitidis | Bacillus spp. |
| Haemophilus influenzae | Nutley 503-1156 | - | - | - | - | - | - |
| Streptococcus pneumoniae | ATCC 6303 | + | - | - | - | - | - |
| Escherichia coli | ATCC 11775 | - | + | - | - | - | - |
| Listeria monocytogenes | G0282 | - | - | + | - | - | - |
| S. agalactiae | ATCC 13813 | - | - | - | + | - | - |
| S. mitis | NCTC 3165 | + | N.D. | N.D. | - | N.D. | - |
| S. milleri | 4224 | - | N.D. | N.D. | - | N.D. | - |
| S. equi | NCTC 9682 | - | N.D. | N.D. | - | N.D. | - |
| Neisseria meningitidis serotype A | ATCC 13077 | N.D. | N.D. | N.D. | N.D. | + | N.D. |
| serotype A | CDC | N.D. | N.D. | N.D. | N.D. | + | N.D. |
| serotype B | CDC | N.D. | N.D. | N.D. | N.D. | + | N.D. |
| serotype C | CDC | N.D. | N.D. | N.D. | N.D. | + | N.D. |
| serotype Y | CDC | N.D. | N.D. | N.D. | N.D. | +| | N.D. |
| serotype W135 | CDC | N.D. | N.D. | N.D. | N.D. | + | N.D. |
| N. polysaccharea | ATCC 43768 | N.D. | N.D. | N.D. | N.D. | + | N.D. |
| N. gonorrhoeae kochii | NRL 32895 | N.D. | N.D. | N.D. | N.D. | +| | N.D. |
| N. cinerea | CDC 10050 | N.D. | N.D. | N.D. | N.D. | + | N.D. |
| N. sicca | Rush isolate | N.D. | N.D. | N.D. | N.D. | + | N.D. |
| Eikenella corrodens | ATCC 23834 | N.D. | N.D. | N.D. | N.D. | + | N.D. |
| Bacillus subtilis | Nutley 558 | - | - | - | - | - | + |
| Corynebacterium pseudotuberculosis | ATCC 19410 | - | - | - | - | - | - |
| C. jeikeium | ATCC 43734 | N.D. | N.D. | N.D. | N.D. | N.D. | N.D. |
| C. genitalium | ATCC 33030 | N.D. | N.D. | N.D. | N.D. | N.D. | N.D. |
| C. xerosis | ATCC 373 | N.D. | N.D. | N.D. | N.D. | N.D. | N.D. |
| Propionibacterium acnes | ATCC 6919 | - | - | - | - | - | - |

FIG. 4C

| Format II Specificity Testing | | | | | | | |
|---|---|---|---|---|---|---|---|
| | | PROBE VP111 | PROBE RDR140 | PROBE RDR230 | PROBE VP109 | PROBE COR28 | PROBE COR48 |
| SPECIES | REFERENCE | S. pneumoniae | E. coli/enteric | L. monocytogen. | S. agalactiae | N. meningitidis | Bacillus spp. |
| Staphylococcus epidermidis | Basel 4233 | - | - | - | - | - | - |
| S. capitis capitis | ATCC 35661 | N.D. | N.D. | N.D. | N.D. | N.D. | - |
| S. cohnii | ATCC 35662 | N.D. | N.D. | N.D. | N.D. | N.D. | - |
| S. haemolyticus | ATCC 29970 | N.D. | N.D. | N.D. | N.D. | N.D. | - |
| S. saprophyticus | ATCC 15305 | N.D. | N.D. | N.D. | N.D. | N.D. | - |
| S. warneri | ATCC 27836 | N.D. | N.D. | N.D. | N.D. | N.D. | - |
| S. auricularis | ATCC 33753 | N.D. | N.D. | N.D. | N.D. | N.D. | - |
| S. saccharolyticus | ATCC 14953 | N.D. | N.D. | N.D. | N.D. | N.D. | - |
| S. aureus | Basel 4247 | - | - | - | - | - | - |
| Mycobacterium tuberculosis | UCSF isolate | - | - | - | - | - | - |
| Mycobacterium intracellulare | UCSF isolate | - | - | - | - | - | - |

FIG. 4D

| Format II Specificity Testing | | PROBE COR36 | PROBE COR44 | PROBE COR02/05 | PROBE COR26 | PROBE COR38 |
|---|---|---|---|---|---|---|
| SPECIES | REFERENCE | Corynebacterium | Propionibacterium | coag.neg.Staph | S. aureus | Mycobacterium |
| Haemophilus influenzae | Nutley 503-1156 | - | - | - | - | - |
| Streptococcus pneumoniae | ATCC 6303 | - | - | - | - | - |
| Escherichia coli | ATCC 11775 | - | - | - | - | - |
| Listeria monocytogenes | G0282 | - | - | - | - | - |
| S. agalactiae | ATCC 13813 | - | - | - | - | - |
| S. mitis | NCTC 3165 | - | N.D. | N.D. | N.D. | N.D. |
| S. milleri | 4224 | - | N.D. | N.D. | N.D. | N.D. |
| S. equi | NCTC 9682 | - | - | - | - | - |
| Neisseria meningitidis serotype A | ATCC 13077 | N.D. | N.D. | N.D. | N.D. | N.D. |
| serotype A | CDC | N.D. | N.D. | N.D. | N.D. | N.D. |
| serotype B | CDC | N.D. | N.D. | N.D. | N.D. | N.D. |
| serotype C | CDC | N.D. | N.D. | N.D. | N.D. | N.D. |
| serotype Y | CDC | N.D. | N.D. | N.D. | N.D. | N.D. |
| serotype W135 | CDC | N.D. | N.D. | N.D. | N.D. | N.D. |
| N. polysaccharea | ATCC 43768 | N.D. | N.D. | N.D. | N.D. | N.D. |
| N. gonorrhoeae kochii | NRL 32895 | N.D. | N.D. | N.D. | N.D. | N.D. |
| N. cinerea | CDC 10050 | N.D. | N.D. | N.D. | N.D. | N.D. |
| N. sicca | Rush isolate | N.D. | N.D. | N.D. | N.D. | N.D. |
| Eikenella corrodens | ATCC 23834 | N.D. | N.D. | N.D. | N.D. | N.D. |
| Bacillus subtilis | Nutley 558 | - | - | - | - | - |
| Corynebacterium pseudotuberculosis | ATCC 19410 | + | - | - | - | ± |
| C. jeikeium | ATCC 43734 | + | N.D. | N.D. | N.D. | N.D. |
| C. genitalium | ATCC 33030 | + | N.D. | N.D. | N.D. | N.D. |
| C. xerosis | ATCC 373 | + | N.D. | N.D. | N.D. | N.D. |
| Propionibacterium acnes | ATCC 6919 | - | + | - | - | - |
| Staphylococcus epidermidis | Basel 4233 | - | - | + | - | - |

FIG. 4E

| Format II Specificity Testing | | PROBE COR36 | PROBE COR44 | PROBE COR02/05 | PROBE COR26 | PROBE COR38 |
|---|---|---|---|---|---|---|
| SPECIES | REFERENCE | Corynebacterium | Propionibacterium | coag.neg.Staph | S. aureus | Mycobacterium |
| S. capitis capitis | ATCC 35661 | - | N.D. | + | - | - |
| S. cohnii | ATCC 35662 | - | N.D. | - | + | - |
| S. haemolyticus | ATCC 29970 | - | N.D. | + | - | - |
| S. saprophyticus | ATCC 15305 | - | N.D. | + | - | - |
| S. warneri | ATCC 27836 | - | N.D. | +/- | - | - |
| S. auricularis | ATCC 33753 | - | N.D. | + | - | - |
| S. saccharolyticus | ATCC 14953 | - | - | - | - | - |
| S. aureus | Basel 4247 | - | - | - | + | - |
| Mycobacterium tuberculosis | UCSF isolate | +/- | - | - | - | + |
| Mycobacterium intracellulare | UCSF isolate | +/- | - | - | - | + |

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GTATTCACCG CGGCATGCTG ATCCG 25

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TATTCACCGC GGCATGCTGA T 21

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AGTAACCATT TGGAGCTAGC CGT 23

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CGGCTAGCTC CAAAAGGTTA CTCTA     25

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CGGCTAGCTC TAAAAGGTTA CTCTA     25

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CGACGGCTAG CTCCAAATGG TTACT     25

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CACATGCTAC AAGGGTCGGT ACAGT     25

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ACTGTACCGA CCATTGTAGC ATGTG     25

( 2 ) INFORMATION FOR SEQ ID NO:9:

( i ) SEQUENCE CHARACTERISTICS:

( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

GGCGCTTACC ACTTTGTGAT TCATG 25

( 2 ) INFORMATION FOR SEQ ID NO:10:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

GGAGTGGGTT GTACCAGAAG TAGAT 25

( 2 ) INFORMATION FOR SEQ ID NO:11:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

CTAATCCCAT AAAACTATTC TCAGT 25

( 2 ) INFORMATION FOR SEQ ID NO:12:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

CGGTACAAAG GGCTGCGATG CCG 23

( 2 ) INFORMATION FOR SEQ ID NO:13:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

GCAAGGAGCC CGCTTACCAC GGTAT 25

( 2 ) INFORMATION FOR SEQ ID NO:14:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

AAGCCGCGAG GCGGAGCCAA TCT     23

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GAGACCGGCT TTCCGAGATT CGCTC     25

( 2 ) INFORMATION FOR SEQ ID NO:16:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CCAACTTTCA TGACTTGACG GG     22

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GGTGTGTACA AGCCCCGGGA ACGTA     25

( 2 ) INFORMATION FOR SEQ ID NO:18:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GCCGGTGGAG TAACCTTTTA GGAGC     25

( 2 ) INFORMATION FOR SEQ ID NO:19:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

CCGGTGGAGT AACCTTTTAG GA     22

( 2 ) INFORMATION FOR SEQ ID NO:20:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

TTGCGACTCG TTGTACCAAC CATTG 25

( 2 ) INFORMATION FOR SEQ ID NO:21:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

AACTGAGATT GGCTTTAAGA GATTA 25

( 2 ) INFORMATION FOR SEQ ID NO:22:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

TAATCTCTTA AAGCCAATCT CAGTT 25

( 2 ) INFORMATION FOR SEQ ID NO:23:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

CCGAACTGAG ACTGGCTTTA AGAGA 25

( 2 ) INFORMATION FOR SEQ ID NO:24:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

AACTGAGACT GGCTTTAAGA GATTA 25

( 2 ) INFORMATION FOR SEQ ID NO:25:

( i ) SEQUENCE CHARACTERISTICS:

(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:25:

AACTGAGACT GGCTTTAAGA GAT    23

(2) INFORMATION FOR SEQ ID NO:26:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:26:

AGGAGGTGAT CCAACCGCA    19

(2) INFORMATION FOR SEQ ID NO:27:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:27:

AACTGGAGGA AGGTGGGGAT    20

(2) INFORMATION FOR SEQ ID NO:28:

(i) SEQUENCE CHARACTERISTICS:
(A) LENGTH: 375 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:28:

GTCATTAGTT GCCATCATTC AGTTGGGCAC TCTAATGAGA CTGCCGGTGA CAAGCCGGAG    60
GAAGGTGGGG ATGACGTCAA GTCCTCATGG CCCTTATGAC CAGGGCTTCA CACGTCATAC    120
AATGGTCGGT ACAGAGGGTA GCCAAGCCGC GAGGCGGAGC CAATCTCACA AAACCGATCG    180
TAGTCCGGAT TGCACTCTGC AACTCGAGTG CATGAAGTCG GAATCGCTAG TAATCGCAGG    240
TCAGCATACT GCGGTGAATA CGTTCCCGGG TCTTGTACAC ACCGCCCGTC ACACCATGGG    300
AGTGGGGGAT ACCAGAAGTA GGTAGGGTAA CCGCAAGGAG CCCGCTTACC ACGGTATGCT    360
TCATGACTGG GGTGA    375

(2) INFORMATION FOR SEQ ID NO:29:

(i) SEQUENCE CHARACTERISTICS:
(A) LENGTH: 386 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:29:

```
TTGCCATCAT TAAGTTGGGC ACTCTAGCGA GACTGCCGGT AATAAACCGG AGGAAGGTGG     60

GGATGACGTC AAATCATCAT GCCCCTTATG ACCTGGGCTA CACACGTGCT ACAATGGTTG    120

GTACAACGAG TCGCAAGCCG GTGACGGCAA GCTAATCTCT TAAAGCCAAT CTCAGTTCGG    180

ATTGTAGGCT GCAACTCGCC TACATGAAGT CGGAATCGCT AGTAATCGCG GATCAGCACG    240

CCGCGGTGAA TACGTTCCCG GGCCTTGTAC ACACCGCCCG TCACCACG AGAGTTTGTA     300

ACACCCGAAG TCGGTGAGGT AACCTTTTAG GAGCCAGCCG CCTAAGGTGG GATAGATGAT   360

TGGGGTGACG TCGTAACAAG GTAGCC                                        386
```

(2) INFORMATION FOR SEQ ID NO:30:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
AGTTGCCATC ATTTAGTTGG GCACTCTAGC GAGACTGCCG GTAATAAACC GGAGGAAGGT     60

GGGGATGACG TCAAATCATC ATGCCCCTTA TGACCTGGGC TACACACGTG CTACAATGGC    120

TGGTACAACG AGTCGCAAGC CGGTGACGGC AAGCTAATCT CTTAAAGCCA GTCTCAGTTC    180

GGATTGTAGG CTGCAACTCG CCTACATGAA GTCGGAATCG CTAGTAATCG CGGATCAGCA    240

CGCCGCGGTG AATACGTTCC CGGGCCTTGT ACACCGCC CGTCACACCA CGAGAGTTTG    300

TAACACCCGA AGTCGGTGAG GTAACCGTAA GGAGCCAGCC GCCTAAGGTG GGATAGATGA   360

TTGGGGTGAA GTCGTAACAA GGTAGC                                         386
```

(2) INFORMATION FOR SEQ ID NO:31:

(i) SEQUENCE CHARACTERISTICS:
        (A) LENGTH: 394 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

```
CTTAAGCTTA GTTGCCATCA TTAAGTTGGG CACTCTAAGT TGACGCCGGT GACAAACCGG     60

AGGAAGGTGG GGATGACGTC AAATCATCAT GCCCCTATG ATTTGGGCTA CACACGTGCT    120

ACAATGGACA ATACAAAGGG Y AGCGAAACC GCGAGGTCAA GCAAATCCCA TAAAGTTGTT   180

CTCAGTTCGG ATTGTAGTCT GCAACTCGAC TATATGAAGC TGGAATCGCT AGTAATCGTA    240

GATCAGCATG CTACGGTGAA TACGTTCCCG GGTCTTGTAC ACACCGCCCG TCACACCACG    300

AGAGTTTGTA ACACCCGAAG CCGGTGGAGT AACCATTTGG AGCTAGCGTC GAAGGTGGGA   360

CAAATGATTG GGGTGAGTCG TAACAAGGTA GCCG                                394
```

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

( x i ) SEQUENCE DESCRIPTION: SEQ ID NO:32:

ACTGAGAATA GTTTTATGGG ATTAG    25

( 2 ) INFORMATION FOR SEQ ID NO:33:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

AGGGTAACCT TTATGGAGCC AGCCG    25

( 2 ) INFORMATION FOR SEQ ID NO:34:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

CGGCTGGCTC CATAAAGGTT ACCCT    25

( 2 ) INFORMATION FOR SEQ ID NO:35:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

ATCTCTTAAA GCCAATCTCA GTT    23

( 2 ) INFORMATION FOR SEQ ID NO:36:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

AACTGAGATT GGCTTTAAGA GAT    23

( 2 ) INFORMATION FOR SEQ ID NO:37:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

GTACAAGGCC CGGGAACGTA TTCACCG    27

( 2 ) INFORMATION FOR SEQ ID NO:38:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:38:

TAACCTTTTA GGAGCCAGCC GCCTA    25

( 2 ) INFORMATION FOR SEQ ID NO:39:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:39:

CCTTTTAGGA GCCAGCCGCC TAAGG    25

( 2 ) INFORMATION FOR SEQ ID NO:40:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:40:

CCTTAGGCGG CTGGCTCCTA AAAGG    25

( 2 ) INFORMATION FOR SEQ ID NO:41:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:41:

CGGTTTCGCT GACCCTTTGT ATTGT    25

( 2 ) INFORMATION FOR SEQ ID NO:42:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:42:

AGGGTAACCT TTATGGAGCC AGCCG    25

( 2 ) INFORMATION FOR SEQ ID NO:43:

( i ) SEQUENCE CHARACTERISTICS:
    ( A ) LENGTH: 28 base pairs
    ( B ) TYPE: nucleic acid

```
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

GACGTCAAAT CATCATGCCC CTTATGTC                                                      28

( 2 ) INFORMATION FOR SEQ ID NO:44:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

GACCTAAGGG CCATGATGAC TTGACGTC                                                      28

( 2 ) INFORMATION FOR SEQ ID NO:45:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

GACATAAGGG CCATGAGGAC TTGACGTC                                                      28

( 2 ) INFORMATION FOR SEQ ID NO:46:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

GGTTAAGTCC CGCAACGAGC GC                                                            22

( 2 ) INFORMATION FOR SEQ ID NO:47:

( i ) SEQUENCE CHARACTERISTICS:
        ( A ) LENGTH: 366 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

GGGCACTCTA AGTTGACNGC CGGTGACAAA CCGGAGGAAG GTGGGGATGA CGTCAAATCA                   60

TCATGCCCCT TATGATTTGG GCTACACACG TGCTACAATG GACAATACAA AGGGCAGCGA                   120

AACCGCGAGG TCAAGCAAAT CCCATAAAGT TGTTCTCAGT TCGGATTGTA GTCTGCAACT                   180

CGACTACATG AAGCTGGAAT CGCTAGTAAT CGTAGATCAG CATGCTACGG TGAATACGTT                   240

CCCGGGTCTT GTACACACCG CCCGTCACAC CACGAGAGTT TGTAACACCC GAAGCCGGTG                   300

GAGTAACCTT TTAGGAGCTA GCNGTCGAAG GTGGACAAA  TGATTGGGGT GAGTCGTAAC                   360

AAGGTA                                                                              366
```

( 2 ) INFORMATION FOR SEQ ID NO:48:

( i ) SEQUENCE CHARACTERISTICS:
        ( A ) LENGTH: 386 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

```
AGTTGCCATC ATTAAGTTGG GCACTCTAGC GAGACTGCCG GTAATAAACC GGAGGAAGGT    60
GGGGATGACG TCAAATCATC ATGCCCCTTA TGACCTGGGC TACACACGTG CTACAATGGT   120
TGGTACAACG AGTCGCAAGC CGGTGACGGC AAGCTAATCT CTTAAAGCCA ATCTCAGTTC   180
GGATTGTAGG CTGCAACTCG CCTACATGAA GTCGGAATCG CTAGTAATCG CGGATCAGCA   240
CGCCGCGGTG AATACGTTCC CGGGCCTTGT ACACACCGCC CGTCACACCA CGAGAGTTTG   300
TAACACCCGA GTCGGTGAGG TAACCTATTA GGAGCCGCCG CCTAAGGTGG GATAGATGAT   360
TGGGGTGAGT CGTAACAAGG TAGCCG                                        386
```

METHODS AND REAGENTS FOR DETECTION OF BACTERIA IN CEREBROSPINAL FLUID

CROSS REFERENCE TO RELATED APPLICATIONS

This application is a continuation-in-part of U.S. Ser. No. 07/738,393, filed Jul. 31, 1991 now abandoned, which is a continuation-in-part of applications U.S. Ser. No. 07/593,176, filed Oct. 5, 1990, now abandoned, and U.S. Ser. No. 07/696,448, filed May 6, 1991 now abandoned.

TECHNICAL FIELD

The present invention relates generally to methods and reagents for identifying and detecting bacteria in cerebrospinal fluid (CSF).

BACKGROUND OF THE INVENTION

In order to treat successfully a disease caused by a bacterium, the rapid and accurate detection and identification of the disease-causing bacterium is required. The detection and identification have traditionally been accomplished by pure culture isolation and identification procedures that make use of knowledge of specimen source, growth requirements, visible (colony) growth features, microscopic morphology, staining reactions, and biochemical characteristics.

A number of different bacterial species can cause meningitis when present in the CSF. The species most frequently causing meningitis include: *Escherichia coli* and other enteric bacteria, *Haemophilus influenzae, Neisseria meningitidis, Streptococcus pneumoniae, Streptococcus agalactiae*, and *Listeria monocytogenes*.

Conventional methods of detection and identification of bacteria in cerebrospinal fluid include the Gram stain, latex agglutination and other antibody-based tests, and culture. The Gram stain and antibody-based tests are rapid (<1 hour), but of low sensitivity (requiring at least $10^4$ colony forming units [CFU]bacteria per ml). Culture methods, while sensitive to approximately 2 CFU per ml, require overnight incubation.

A number of scientific publications relating to this invention exist. For example, the polymerase chain reaction has been used to detect individual species of bacteria causing meningitis: Kuritza and Oehler, May, 1991, *Abstracts of the General Meeting of the ASM* page 84; Deneer and Boychuk, 1991, *Applied Environmental Microbiology* 57: 606–609; and Kristiansen et al., 1991, *Lancet* 337: 1568–1569.

In addition, some of the nucleotide sequence data used herein is available in Genbank. The method of reverse dot-blot detection has been described by Saiki et al., 1989. The use of uracil-N-glycosylase has been described by Longo et al., 1990, *Gene* 93: 125–128.

A method of detecting bacteria in Cerebrospinal Fluid ("CSF") which is both sensitive and rapid would represent a great improvement over current methods of detection. The present invention meets these needs.

SUMMARY OF THE INVENTION

The present invention pertains to methods and reagents for the rapid detection and identification of bacteria in CSF. The detection and identification is based upon the hybridization of nucleotide probes to nucleotide sequences present in a defined species or group of species, but not in others.

2

In a preferred method, a target region from genomic DNA or complementary DNA transcribed from 16S rRNA is amplified and the resultant amplified DNA is treated with a panel of probes. Each probe in the panel can hybridize to the DNA of a different species or group of species of bacteria found in CSF. The probe which successfully hybridizes to the amplified DNA is determined and the bacterium is classified as a particular species or group of species.

The invention also pertains to specific probes and their complements for identifying bacteria found in CSF. It also pertains to unique oligonucleotide sequences, and mutants, fragments and subsequences thereof, from which such specific probes were derived.

As indicated, also contemplated herein is a panel of probes which will allow the detection and identification of bacteria commonly found in CSF. The panel includes probes for the bacteria causing meningitis listed above as well as bacterial species which are commonly considered contaminants of human clinical samples such as blood or cerebrospinal fluid. Such contaminant species are also capable of causing meningitis; however, these organisms do so at a lower frequency than the agents listed in the "Background of the Invention" and include: Bacillus species, Corynebacterium species, *Propionibacterium acnes* and other Propionibacterium species, and *Staphylococcus epidermidis* and other coagulase-negative Staphylococci (*Bergey's Manual of Systematic Bacteriology*, ed. J. G. Holt, Williams and Wilkins, Baltimore, Md., which is incorporated herein by reference).

The panel will also include a probe for a wide range of bacteria, referred to as a "universal bacterial probe," in order to detect species that cause meningitis at a lower frequency but for which there is no specific probe included on the panel. Therefore, this probe will provide confirmation of the detection of pathogens and contaminants as well as detection of species for which there is no specific probe.

Further defined herein are nucleotide sequence data for some of the pathogen and contaminant species in the region of the 16S rRNA. Such nucleotide sequence information for the 16S rRNA gene is not available for some of the above bacterial species. Accordingly, it was necessary to obtain the sequence information experimentally.

The invention further provides methods of amplification and associated reagents for kits containing universal bacterial primers for amplifying a specific universal target region of DNA for all bacteria and probes which hybridize to a nucleotide sequence which is characteristic of a species or group of species of bacteria within that target region.

BRIEF DESCRIPTION OF THE DRAWINGS

FIG. 1 shows nucleotide sequence data for part of the 16S rRNA gene for:

1-1) *Neisseria meningitidis*

1-2) *Streptococcus agalactiae*

1-3) *Streptococcus pneumoniae*

1-4) *Staphylococcus epidermidis*

1-5) *Staphylococcus aureus*

1-6) *Streptococcus pyogenes*

FIG. 2 shows nucleotide sequences and positions of oligonucleotide probes for *Streptococcus agalactiae, Listeria monocytogenes, Streptococcus pneumoniae, Haemophilus influenzae, Neisseria memingitidis, Escherichia coil, Propionibacterium acnes, Staphylococcus epidermidis, Staphylococcus aureus*, Propionibacterium species, Bacillus species, coagulase-negative Staphylococci, and Corynebacterium species.

FIG. 3 shows a summary of data obtained from probe testing against various bacterial DNAs as described in Example 2.

FIG. 4 shows a summary of data obtained from probe testing against various bacterial DNAs as described in Example 4.

DETAILED DESCRIPTION OF THE INVENTION

The present invention is a method for determining the presence of and identifying bacteria by means of hybridizing probes to amplified nucleotide sequences which are characteristic of a species or group of species of bacteria.

The use of specific polynucleotide sequences as probes for the recognition of infectious agents is becoming a valuable alternative to problematic immunological identification assays. For example, PCT publication WO84/02721, published 19 July 1984 describes the use of nucleic acid probes complementary to targeted nucleic acid sequences composed of ribosomal RNA, transfer RNA, or other RNA in hybridization procedures to detect the target nucleic acid sequence. While this assay may provide greater sensitivity and specificity than known DNA hybridization assays, hybridization procedures which require the use of a complementary probe are generally dependent upon the cultivation and/or enrichment of a test organism and are, therefore, unsuitable for rapid diagnosis. Probes can be used directly on clinical specimens if a means of amplifying the DNA or RNA target is available.

Polymerase chain reaction (PCR) is a powerful nucleic amplification technique that can be used for the detection of small numbers of pathogens whose in vitro cultivation is difficult or lengthy, or as a substitute for other methods which require the presence of living specimens for detection. In its simplest form, PCR is an in vitro method for the enzymatic synthesis of specific DNA sequences, using two oligonucleotide primers that hybridize to opposite strands and flank the region of interest in the target DNA. A repetitive series of cycles involving template denaturation, primer annealing, and the extension of the annealed primers by DNA polymerase results in the exponential accumulation of a specific fragment whose termini are defined by the 5' ends of the primers. PCR reportedly is capable of producing a selective enrichment of a specific DNA sequence by a factor of $10^{12}$. The PCR method is described in Saiki et al., 1985, *Science* 230: 1350, and is the subject of U.S. Pat. Nos. 4,683,195, 4,683,202, 4,800,159, and 4,965,188, which are incorporated herein by reference. This method has been used to detect the presence of the aberrant sequence in the beta-globin gene which is related to sickle cell anemia (Saiki et al., 1985, supra.) and human immunodeficiency virus (HIV) RNA (Byrne et al., 1988, *Nuc. Acids Res.* 16: 4165, and U.S. Pat. No. 5,008,182, incorporated herein by reference).

The invention provides methods for determining the presence of a bacterial polynucleotide in a sample suspected of containing said polynucleotide, wherein said polynucleotide contains a selected target region, said method comprising: (a) amplifying the target region, if any, to a detectable level; (b) providing a panel of polynucleotide probes, each containing a sequence which is complementary to a polynucleotide sequence characteristic of a different species or group of species of bacteria in the target region: (c) incubating the amplified target region, if any, with the polynucleotide probes under conditions which allow specificity of hybrid duplexes: and (d) detecting hybrids formed between the amplified target region, if any, and the polynucleotide probes.

The methods of the present invention thus enable determination of the presence of the bacteria more rapidly than heretofore possible with prior art detection methods. The basic PCR process is carried out as follows.

A sample is provided which needs to be tested or is suspected of containing a particular nucleic acid sequence of interest, the "target sequence." The nucleic acid contained in the sample may be first reverse transcribed into cDNA, if necessary, and then denatured, using any suitable denaturing method, including physical, chemical, or enzymatic means, which are known to those of skill in the art. A preferred physical means for strand separation involves heating the nucleic acid until it is completely (>99%) denatured. Typical heat denaturation involves temperatures ranging from about 80° C. to about 150° C., for times ranging from about 5 seconds to 10 minutes using current technology. Methods for the amplification of RNA targets using a thermostable DNA polymerase are described in PCT/US90/07641, filed Dec. 21, 1990, and incorporated herein by reference.

The denatured DNA strands are then incubated with the selected oligonucleotide primers under hybridization conditions, conditions which enable each primer to hybridize to a single-stranded nucleic acid template. As known in the art, the primers are selected so that their relative positions along a duplex sequence are such that an extension product synthesized from one primer, when it is separated from its complement, serves as a template for the extension of the other primer.

The primer must be sufficiently long to prime the synthesis of extension products in the presence of the agent for polymerization. The exact length of the primers will depend on many factors, including temperature, source of the primer and use of the method. For example, depending on the complexity of the target sequence, the oligonucleotide primer typically contains about 15–30 nucleotides, although it may contain more or fewer nucleotides. Short primer molecules generally require cooler temperatures to form sufficiently stable hybrid complexes with the template. The primers must be sufficiently complementary to hybridize selectively with their respective strands.

The primers used herein are selected to be "substantially" complementary to the different strands of each specific sequence to be amplified. The primers need not reflect the exact sequence of the template, but must be sufficiently complementary to hybridize selectively with their respective strands. Non-complementary bases or longer sequences can be interspersed into the primer, provided that the primer retains sufficient complementarity with the sequence of one of the strands to be amplified to hybridize therewith, and to thereby form a duplex structure which can be extended by the agent for polymerization. The non-complementary nucleotide sequences of the primers may include restriction enzyme sites. Appending a restriction enzyme site to the end(s) of the target sequence is particularly helpful for subsequent cloning of the target sequence.

The oligonucleotide primers and probes may be prepared by any suitable method. For example, synthetic oligonucleotides can be prepared using the triester method of Matteucci et al., 1981, *J. Am. Chem. Soc.* 03: 3185–3191. Alternatively automated synthesis may be preferred, for example, on a Biosearch 8700 DNA synthesizer using cyanoethyl phosphoramidite chemistry. Many methods for labelling nucleic acids, whether probe or target, are known in the art and are suitable for purposes of the present invention. Suitable labels may provide signals detectable by fluorescence, radioactivity, colorimetry, X-ray diffraction or absorption, magnetism, enzymatic activity, and the like. Suitable labels include fluorophores, chromophores, radioactive isotopes (particularly $^{32}P$ and $^{125}I$), electrondense reagents, enzymes and ligands having specific binding partners. Enzymes are typically detected by their activity. For example, horse-radish-peroxidase (HRP) can be detected by its ability to convert diaminobenzidine to a blue pigment. A preferred method for HRP based detection uses tetramethylbenzidine (TMB) as described in *Clin. Chem.* 833: 1368 (1987). An alternative detection system is the Enhanced Chemiluminescent (ECL) detection kit commercially available from Amersham. The kit is used in accordance with the manufacturer's directions.

Primers and probes are typically labeled with radioactive phosphorous $^{32}P$ by treating the oligonucleotides with polynucleotide kinase in the presence of radiolabeled ATP. However, for commercial purposes non-radioactive labeling systems may be preferred, such as, horseradish peroxidase-avidin-biotin or alkaline phosphatase detection systems. If the primer or one or more of the dNTPs utilized in a PCR amplification has been labeled (for instance, the biotinylated dUTP derivatives described by Lo et al., 1988, *Nuc. Acids Res.* 16: 8719) instead of the probe, then hybridization can be detected by assay for the presence of labeled PCR product. Biotinylated primers can be prepared by direct biotinylation of the oligonucleotide. For 5' biotinylation of oligonucleotides during direct solid phase synthesis biotin-containing phosphoramidites were used according to Alves et al., 1989, *Tetra. Let* 30: 3098: Cocuzza, 1989, *Tetra Let.* 30: 6287; and Barabino et al., 1989, *EMBO J.* 8: 4171. Solid phase synthesis of biotinylated oligonucleotides at any internal or terminal (5' or 3') position is also suitable for preparing biotinylated primers and probes (Pieles et al., 1989, *NAR* 18: 4355, and Misiura et al., 1989, *NAR* 18: 4345). Alternatively, primers can be biotinylated using terminal deoxynucleotide transferase (TdT) (Boeringer Mannheim).

Template-dependent extension of the oligonucleotide primer(s) is catalyzed by a polymerizing agent in the presence of adequate amounts of the four deoxyribonucleoside triphosphates (dATP, dGTP, dCTP, and dTTP) or analogs such as dUTP, in a reaction medium which is comprised of the appropriate salts, metal cations, and pH buffering system. Suitable polymerizing agents are enzymes known to catalyze primer- and template-dependent DNA synthesis. Known DNA polymerases include, for example, *E. coli* DNA polymerase I or its Klenow fragment, $T_4$ DNA polymerase, *Taq* DNA polymerase, DNA polymerase from *Pyrococcus furiosus, Thermus thermophilus (Tth), Thermotoga maritima, Thermosipho africanus*, and DNA polymerase from *Thermococcus litoralis*. The reaction conditions for catalyzing DNA synthesis with these DNA polymerases are well known in the art.

The products of the synthesis are duplex molecules consisting of the template strands and the primer extension strands, which include the target sequence. These products, in turn, serve as templates for another round of primer extension. In the second cycle, the primer extension strand of the first cycle is annealed with its complementary primer; synthesis yields a "short" product which is bounded on both the 5'-and the 3'-ends by primer sequences of their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve.

The PCR method can be performed in a number of temporal sequences. For example, it can be performed step-wise, where after each step new reagents are added, or in a fashion where all of the reagents are added simultaneously, or in a partial step-wise fashion, where fresh reagents are added after a given number of steps.

In a preferred method, the PCR reaction is carried out as an automated process which utilizes a thermostable enzyme. In this process the reaction mixture is cycled through a denaturing step, a primer annealing step, and a synthesis step. A DNA thermal cycler specifically adapted for use with a thermostable enzyme may be employed, which utilizes temperature cycling without a liquid-handling system, thereby eliminating the need to add the enzyme at every cycle. This type of machine is commercially available from Perkin Elmer (Norwalk, Conn.).

After amplification by PCR, the target polynucleotides may be detected directly by gel analysis provided the target DNA is efficiently amplified and the primers are highly specific to the target region to be amplified. To assure PCR efficiency, glycerol and other related solvents such as dimethyl sulfoxide, can be used to increase the sensitivity of the PCR at the amplification level and to overcome problems pertaining to regions of DNA having strong secondary structure. These problems may include (1) low efficiency of the PCR, due to a high frequency of templates that are not fully extended by the polymerizing agent or (2) incomplete denaturation of the duplex DNA at high temperature, due to high GC content. The use of such solvents can increase the sensitivity of the assay at the level of amplification to approximately several femtograms of DNA (which is believed to correspond to a single bacterial cell). This level of sensitivity eliminates the need to detect amplified target DNA using a probe, and thereby dispenses with the requirements for labeling of probes, gel electrophoresis, Southern blotting, filter hybridization, washing and autoradiography. The concentration range for glycerol is about 5%–20% (v/v), and the DMSO concentration range is about 3%–10% (v/v).

Alternatively, the target polynucleotides may be detected by hybridization with a polynucleotide probe which forms a stable hybrid with that of the target sequence under high to low stringency hybridization and wash conditions. An advantage of detection by hybridization is that, depending on the probes used, additional specificity is possible. If it is expected that the probes will be completely complementary (i.e., about 99% or greater) to the target sequence, high stringency conditions will be used. If some mismatching is expected, for example if variant strains are expected with the result that the probe will not be completely complementary, the stringency of hybridization may be lessened. However, conditions are chosen which rule out nonspecific/adventitious binding. Conditions which affect hybridization and which select against nonspecific binding are known in the art (*Molecular Cloning A Laboratory Manual*, second edition, J. Sambrook, E. Fritsch, T. Maniatis, Cold Spring Harbor Laboratory Press, 1989) Generally, lower salt concentration and higher temperature increase the stringency of binding. For example, in general, stringent hybridization conditions include incubation in solutions which contain approximately 0.1×SSC, 0.1% SDS, at about 65° C. incubation/wash temperature, and moderately stringent conditions are incubation in solutions which contain approximately 1–2×SSC, 0.1% SDS and about 50° C.–65° C. incubation/wash temperature. Low stringency conditions are 2×SSC and about 30° C.–50° C.

Stringency requirements can be modified to alter target specificity as described. For example, where *Staphylococcus aureus* is to be detected, it is well within the scope of the invention for those of ordinary skill in the art to modify the stringency conditions described above and cause other Staphylococcus species to be excluded or included as targets. The novel 16S rRNA sequences provided herein are suitable for preparing a vast number of probe compounds having particular hybridization characteristics as desired.

An alternate method of hybridization and washing is to perform a low stringency hybridization (5×SSPE, 0.5% SDS) followed by a high stringency wash in the presence of 3M tetramethyl-ammonium chloride (TMACl). The effect of the TMACl is to equalize the relative binding of A-T and G-C base pairs so that the efficiency of hybridization at a given temperature corresponds more closely to the length of the polynucleotide. Using TMACl, it is possible to vary the temperature of the wash to achieve the level of stringency desired. (See Base composition-independent hybridization in tetramethylammonium chloride: A method for oligonucleotide screening of highly complex gene libraries (Wood et al., 1985, *Proc. Natl. Acad. Sci. USA* 82: 1585–1588, incorporated by reference herein).

Probes for bacterial target sequences may be derived from the 16S rRNA gene sequences or their complements. The probes may consist of the bases A, G, C or T or analogs (including inosine and 5-methyl-cytosine). The probes may be of any suitable length which spans the target region and which allows specific hybridization to the target region. As used herein "specific hybridization" refers to that hybridization pattern or character suitable for accurately identifying bacterial agents present in a sample. In a preferred embodiment, the invention is suitable for use as a panel array of probes. Consequently, the specific hybridization pattern for the panel is a composite of individual specific hybridization probes, which probes may individually include or exclude particular species, subtypes, or genera as desired. Thus, it may be preferable to prepare probes for specifically identifying each of *Streptococcus agalactiae* and *S. pneumoniae*. Alternatively, it may be suitable to prepare one probe for detecting any Streptococcus species.

Generally, the probes will have at least 14 nucleotides, preferably at least 18 nucleotides, and more preferably at least 20 to 30 nucleotides of either of the complementary DNA target strands. If there is to be complete complementarity, i.e., if the strain contains a sequence identical to that of the probe, the duplex will be relatively stable under even stringent conditions and the probes may be short, i.e., in the range of about 10–30 base pairs. If some degree of mismatch is expected with the probe, i.e., if it is suspected that the probe will hybridize to a variant region, or to a group of sequences such as all species within a specific genus, e.g., Bacillus species, the probe may be of greater length (i.e., 15–40 bases) to balance the effect of the mismatch(es).

The probe may be formed from a subset of the target region and therefore need not span the entire target region. Any subset of the target region has the potential to specifically identify the target region. Consequently, the nucleic acid probe may be 10–40 nucleotides in length and hybridize to as few as 10 nucleotides of the target region. Further, fragments of the probes may be used so long as they are sufficiently characteristic of the bacterial species to be detected. If desired, the probe may also be labeled. A variety of labels which would be appropriate, as well as methods for their inclusion in the probe are known in the art and include, for example, radioactive atoms, such as $^{32}P$, or other recognizable functionalities, e.g., biotin (preferably using a spacer arm), fluorescent dyes, electrondense reagents, enzymes capable of forming easily detectable reaction products (e.g., alkaline phosphatase and horseradish peroxidase), or antigens for which specific antisera or monoclonal antibodies are available. The probe may also be modified for use in a specific format such as the addition of 100–150 T residues for reverse dot blot or the conjugation to Bovine serum albumin for the method of Longiaru et al. described below.

It may be desirable to determine the length of the PCR product detected by the probe. This may be particularly true if it is suspected that variant bacterial strains may contain deletions or insertions within the target region, or if one wishes to confirm the length of the PCR product In such circumstances, it is preferable to subject the products to size analysis as well as hybridization with the probe. Methods for determining the size of nucleic acids are known in the art, and include, for example, gel electrophoresis, sedimentation in gradients, and gel exclusion chromatography.

In order to obtain probes to be used for the PCR assays described herein, enough of the nucleotide sequence of the target region must be known. Analysis of the nucleotide sequence of the target region may be by direct analysis of the PCR amplified products as described in Gyllensten and Erlich, 1988, *Proc. Natl. Acad. Sci. USA* 85: 7652, and in U.S. Pat. Nos. 5,065,584 and 5,075,216, which are incorporated herein by reference. A modification of this procedure involves separating the duplex DNA strands of the target region and generating a single stranded DNA template for use in the sequencing reactions (Mitchell and Merrill, 1989, *Analytical Biochemistry* 178: 239–242).

One embodiment of the present invention is the discovery Of the nucleotide sequence data for the target regions (16S rRNA genes) obtained experimentally for the following organisms: *Neisseria meningitidis* (SEQ ID No. 28) *Streptococcus pneumoniae* (SEQ ID No. 30) and *Streptococcus agalactiae* (SEQ ID No. 29) and *Staphylococcus epidermidis* (SEQ ID No. 31), *Streptococcus pyogenes* (SEQ ID No. 48), and *Staphylococcus aureus* (SEQ ID No. 47). In FIG. 1—1 through 1—6 an "R" indicates A or G; "Y" indicates C or T; and "N" indicates A, G, T, or C. This information unexpectedly provided the nucleotide sequence variability on which the species-specific or group-specific probes were based. Fragments, subsequences, complements, or transcripts of these nucleotide sequences will also be useful for design of these probes. For example, methods for preparing probes for hybridizing to detect the novel 16S RNA nucleic acid sequences provided are disclosed herein. Suitable subsequence lengths for target-specific detection are between 14 and 400 nucleotides. The novel sequences are also suitable for preparing primers for amplification of the 16S rRNA target nucleic acids.

Diagnosis of bacterial meningitis using PCR is possible using a number of different strategies. The following features of bacterial meningitis are relevant to the design of a diagnostic assay: (1) since CSF is a normally sterile body fluid, any level of infection by any species of bacteria can result in meningitis; (2) since, in a given CSF sample from a patient with meningitis, one or more of a number of different bacterial species may be present, any one species representing a clinical problem, it is important to be able to detect the presence of more than one bacterial species in the sample; and (3) the optimal antibiotic treatment varies depending on the type of bacterial species causing the meningitis. Hence, it is clinically useful to be able to differentiate the individual species or groups of species capable of causing meningitis.

One approach to diagnosing bacterial meningitis is to run several different individual PCR assays. PCR detection of individual species of bacteria causing meningitis has been described in the scientific literature. For example, Kuritza and Oehler, May, 1991, *Abstracts of the General Meeting of the ASM* page 84; Deneer and Boychuk, 1991, *Applied and Environmental Microbiology* 57: 606–609; and Kristiansen, 1991, *Lancet* 337: 1568–1569.

Another approach, which is a preferred embodiment of the present invention, is to run a single PCR assay utilizing universal bacterial PCR primers and a panel of probes. Each probe is specific to a species or group of species which are commonly found in CSF and will preferably be used simultaneously with other probes. The universal bacterial primers correspond to highly conserved regions of a gene found in most bacteria and hence are capable of amplifying the target gene of most bacterial species. In a preferred embodiment, the primers used are those described in co-pending application, Ser. No. 07/696,448 incorporated herein by reference. These primers, RW01 (SEQ ID No. 27) 5'-AACTGGAGGAAGGTGGGGAT-3' and DG74 (SEQ ID No. 26) 5'-AGGAGGTGATCCAACCGCA-3', yield an approximately 370 base pair PCR product corresponding to base pairs 1170 to 1540 of the *E. coli* 16S rRNA gene. This target region is of sufficient length to encompass two regions of high variability characterized for the 16S rRNA gene, variable regions 8 and 9. The variability in these regions may encompass probes which are to some degree specific to the various species and groups of species of bacteria found in CSF.

The degree of specificity desired for each probe is dictated by two major considerations (1) the probe should be broad enough in range to detect most of the strains of a given species which are found in clinical samples and (2) the probe should be narrow enough in range to exclude closely related species that are commonly found in cerebrospinal fluid. In some cases, a probe that is broad in range and detects some closely related species that are not found in cerebrospinal fluid is preferable to a narrower range probe that may not detect all the strains desired. Information on (1) the types of bacterial species found in cerebrospinal fluid and (2) species closely related to a given species are described in *Bergey's Manual of Systematic Bacteriology* (ed. J. G. Holt, Williams and Wilkins, Baltimore, Md.) and *The Manual of Clinical Microbiology* (ed. A. Balows, American Society for Microbiology, Washington, D.C.).

For the probes described, the prior art, while providing guidelines for the characteristics of optimal probes (such as the sequence in comparison to available nucleotide sequence data, a low degree of secondary structure and optimal length) does not provide a means of predicting the experimental performance of probes for detecting bacteria found in CSF. This information must be discovered empirically by hybridization testing of many different isolates of the pathogens and of closely related species, as illustrated in the examples below. The nucleotide sequences described in FIG. 2 provide preferred embodiments of the invention. However, providing the specific sequences and methods shown herein, one of ordinary skill in the art is enabled to prepare additional probes that are within the scope of the present invention.

In addition to probes which allow species- or group-specific identification of bacteria, the panel of probes would also preferably include a universal bacterial probe capable of specifically hybridizing to the amplified target region of any bacterial species (RDR245, 5'-GTACAAGGCCCGGGAACGTATTCACCG-3' [SEQ ID No. 37], described in copending application Ser. No. 07/696,448, filed May 6, 1991 now abandoned, incorporated herein by reference). This universal bacterial probe detects the presence of bacteria not detected by the more specific probes of the invention such as species representing less common causes of meningitis, for example, *Flavobacterium meningosepticum*, etc. The panel of probes preferably includes probes of bacterial species commonly considered contaminants of clinical samples, such as Corynebacterium species, Bacillus species, Propionibacterium species, and coagulase-negative Staphylococci. The panel could also include other probes which are relatively broad in their range of detection, such as RW03 (SEQ ID No. 43), for gram-positive bacteria, and RDR476 (SEQ ID No. 44) and RDR477 (SEQ ID No. 45), which used together detect gram-negative bacteria other than Flauobacteria and Bacteroides.

RW03 SEQ ID No. 43 5'-GACGTCAAATCATCATGCCCCTTATGTC-3'
RDR476 SEQ ID No. 44 5'-GACCTAAGGGCCATGATGACTYGACGTC-3'
RDR477 SEQ ID No. 45 5'-GACATAAGGGCCATGAGGACTTGACGTC-3'

The presence of the target sequence in a biological sample is detected by determining whether a hybrid has been formed between the probe and the nucleic acid subjected to the PCR amplification techniques. Methods to detect hybrids formed between a probe and a nucleic acid sequence are known in the art. For example, an unlabeled sample may be transferred to a solid matrix to which it binds, and the bound sample subjected to conditions which allow specific hybridization with a labeled probe: the solid matrix is then examined for the presence of the labeled probe. In the disclosed embodiments of the invention where the hybridization target nucleic acids, i.e., PCR product DNA, is fixed to a solid support, the term Format I may be used to describe such a detection scheme.

Alternatively, if the sample is labeled, an unlabeled probe is bound to the matrix, and after exposure to the labeled sample under the appropriate hybridization conditions, the matrix is examined for the presence of a label. Saiki et at., 1989, *Proc. Natl. Acad. Sci. USA* 86: 6230–6234, which is incorporated herein by reference, describe methods of immobilizing multiple probes on a solid support and using hybridization to detect the amplified target polynucleotides of interest (see also copending U.S. Ser. No. 07/414,542, filed Sep. 29, 1989, U.S. Pat. No. 5,232,829 which is incorporated herein by reference).

The latter two procedures are well suited to the use of a panel of probes which can provide simultaneous identification of more than one pathogen or contaminant in a single clinical sample. As used herein, "Format II" refers to a detection scheme wherein the oligonucleotide probe is fixed to a solid support. In another alternative procedure, a solution phase sandwich assay may be used with labeled polynucleotide probes, and the methods for the preparation of such probes are described in U.S. Pat. No. 4,820,630, issued Apr. 11, 1989, which is incorporated herein by reference.

Therefore, the probes described below are preferably applied to the detection of meningitis by using them in combination to detect and identify what bacteria are present in a sample of cerebrospinal fluid. All of the probes described below, as well as additional probes, can be arranged in a reverse dot blot format, as described by Saiki et al., (supra.) Each of the probes is immobilized as a separate dot on a solid support such as a nylon membrane or microtiter plate. The amplified DNA is hybridized to each of the probes at the same time in an aqueous solution. The pattern of the signals from each of the dots (i.e., probes) indicates the identity of the target DNA. Accordingly, upon amplification of the target region (preferably by PCR), and application of the panel of probes described herein, hybridization of one or more of the probes in the panel (including the universal probe when applied to CSF) will result in a positive signal and the positive identification of the bacterial species present as either *Listeria monocytogenes, E. coli/ enteric bacteria, Haemophilus influenzae, Neisseria meningitidis, Streptococcus pneumoniae, S. agalactiae, Staphylococcus epidermidis, Propionibacterium acnes,* Propionibacterium species, Bacillus species, coagulase-negative Staphylococci, Corynebacterium species, *Staphylococcus aureus*, or a bacterium which does not react with any of the more specific probes.

Those skilled in the art will also be aware of the problems of contamination of a PCR by the amplified nucleic acid from previous reactions and non-specific amplification. Methods to reduce these problems are provided in PCT patent application Ser. No. 91/05210, filed Jul. 23, 1991, incorporated herein by reference. The method allows the enzymatic degradation of any amplified DNA from previous reactions and reduces non-specific amplification. The PCR amplification is carried out in the presence of dUTP instead of dTTP. The resulting double-stranded uracil-containing product is subject to degradation by uracil N-glycosylase (UNG), whereas normal thymine-containing DNA is not degraded by UNG. Adding UNG to the amplification reaction mixture before the amplification is started degrades all uracil-containing DNA that might serve as target. Because the only source of uracil-containing DNA is the amplified product of a previous reaction, this method effectively sterilizes the reaction mixture, eliminating the problem of contamination from previous reactions (carryover). UNG itself is rendered temporarily inactive by heat, so the denaturation steps in the amplification procedure also serve to inactivate the UNG. New amplification products, therefore, though incorporating uracil, are formed in an effectively UNG-free environment and are not degraded.

Also within the scope of the present invention are amplification and detection kits for use in carrying out any of the aforementioned amplification and detection processes. The diagnostic kits include the polynucleotide probes and the primers in separate containers. Either of these may or may not be labeled. If unlabeled, the ingredients for labeling may also be included in the kit. The kit may also contain other suitably packaged reagents and material needed for the particular hybridization protocol, for example, standards, and/or polymerizing agents, as well as instructions for conducting the test.

In use, the components of the PCR kit, when applied to a nucleic acid sample, create a reagent mixture which enables the detection and amplification of the target nucleic acid sequence. The reagent mixture thus includes the components of the kit as well as a nucleic acid sample which contains the polynucleotide chain of interest. The teachings of the references cited in the present application are incorporated herein by reference.

A variation of this invention is to use an alternate method of producing the amplified target region. For example, the TAS amplification system, (Kwoh et al., 1989, *Proc. Natl. Acad. Sci. USA* 86: 1173–177) and its modification, SSSR (Guatelli et al., 1990, *Proc. Nat. Acad. Sci. USA* 87: 1874–1878) is a method for amplifying RNA or DNA templates using cycles consisting of a cDNA step to produce a cDNA copy of an RNA template, and an RNA transcription step to increase the copy number of the cDNA or DNA template. This method, like PCR, employs two oligonucleotide primers which hybridize to opposite strands of the target region and flank the target region. The universal bacterial primers described herein may, with minor modifications (the addition of RNA polymerase promoter sequences at the 5' end of one of the primers), be used in a TAS or SSSR amplification system. The subsequent step of the assay, detection by the oligonucleotide probes described herein, may be carried out essentially as described above for the PCR-based assay or may be done using a bead-based sandwich hybridization system (Kwoh et al.).

The nucleotide sequence data described herein can also provide specific detection of bacterial species when used in other nucleic acid-based assays. For example, the nucleotide sequence information discovered for *S. pneumoniae* and *S. agalactiae* indicated that there is a single base-pair mismatch between these two organisms in the region of the *S. pneumoniae* probe RDR224 (SEQ ID No. 23). This mismatch could be used in a ligase chain reaction system to provide discrimination between these two organisms in a clinical sample (Wu and Wallace, 1988, *Genomics* 4: 560–569). The ligase chain reaction involves the use of two sets of oligonucleotide primers. Each primer within the set is complementary to the other. The different sets of primers are located directly adjacent to each other along the template. A single base pair mismatch in between the two sets of primers disrupts the reaction, whereas a perfect match between the primer sets and the template results in target amplification. In another example, the sequence of probes described herein could be used to design corresponding probes in a signal amplification system such as the Q beta replicase system (Kramer and Lizardi, 1989, *Nature* 339: 401–402, and Lomeli et al., 1989, *Clin. Chem.* 35: 1826–1831). This system involves an RNA probe containing the specific probe sequence inserted into the MDV-1 variant of the Q-beta RNA genome. The RNA probe is replicated using Q-beta replicase, producing up to $10^{12}$ molecules per reaction, after hybridization of the probe to the sample to be assayed.

By way of further specificity, the following probe and primer nucleotide sequence data is provided:

Primer DG74 (SEQ ID No. 26) corresponds to the complement of nucleotide base numbers 1522–1540 in the *E. coli* 16S ribosomal RNA gene as specified in Neefs supra.

Primer RW01 (SEQ ID No. 27) corresponds to nucleotide base numbers 1170–1189 in the *E. coil.* 16S ribosomal RNA gene as specified in Neefs supra.

Further, FIG. 1 provides a description of nucleotide sequences isolated as described below, which can be used to design and formulate probes and primers corresponding to fragments or subsequences thereof or their complements.

Oligonucleotide probes for various bacterial species are shown in FIG. 2.

The following examples are intended to be illustrative of the various methods and compounds of the invention.

EXAMPLE 1

Methods Used to Obtain Sequence Data and Design Probes

A. DNA Sequencing Protocol

In order to obtain the DNA sequence from the bacterial species desired, it was necessary to (1) amplify the amount of the target region present and then (2) isolate the individual DNA strands (single-stranded DNA) for use in the sequencing reactions.

DNA was prepared from cell pellets of various bacterial species by treatment with lysozyme, SDS and proteinase K according to the method of Silhavy et al. (Silhavy, T. J., M. L. Berman, and L. W. Enquist, 1984, Experiments with gene fusions, pages 137–139. Cold Spring Harbor Laboratory, Cold Spring Harbor, N.Y.). Bacterial strains were obtained in the form of cell pellets (frozen or non-frozen). The concentration of DNA in the preparations was estimated by gel electrophoresis. Ten ng amounts of DNA were amplified in two different ways. One set of PCR reactions utilized a biotinylated PL06 (5'-GGTTAAGTCCCGCAACGAGCGC [SEQ ID No. 46]) and nonbiotinylated DG74 (SEQ ID No. 26) whereas the other set of reactions utilized nonbiotinylated PL06 and biotinylated DG74 (SEQ ID No. 26). The conditions used for the amplifications were as described in Example 2, except that the number of cycles was 25 and an annealing temperature of 60° C. rather than 55° C. was used for DNA from *S. agalactiae*, *S. epidermidis*, *S. pneumoniae*, and *L. monocytogenes*, *S. aureus*, and *S. pyogenes*.

For the preparation of single-stranded DNA to use as a template in the sequencing reactions, two methods were used. One method was based on the use of streptavidin agarose beads and was used for the sequencing of *S. agalactiae* and *S. pneumoniae* (Mitchell and Merrill, 1989, *Analytical Biochemistry* 178: 239–242). The other was based on the use of streptavidin linked to magnetic beads and was used for sequencing of *N. meningitidis*, *S. epidermidis*, *S. aureus*, and *S. pyogenes* (Bowman and Palumbi, Molecular Evolution: Producing the Biochemical Data, [A Volume of Methods in Enzymology], Zimmer et al., eds. [in press]). In the first method, 90 μl of the amplified DNA was combined with 200 μl of streptavidin agarose slurry (Bethesda Research Laboratories, catalog #59442SA) in a 2.0 ml microcentrifuge tube. The mixture was incubated at room temperature for 30 minutes or more, mixing frequently or rotating on a Labquake apparatus. The mixture was spun in an Eppendorf 5415 microfuge for 10 seconds at speed setting #1. The supernatant was removed. The pellet was washed with 500 μl of TE (10 mM Tris-HCl, 1 mM EDTA, pH 8.0) by shaking gently or Labquaking for 1 minute. The mixture was spun in the microfuge for 10 seconds at speed setting #1. The supernatant was removed. The TE wash was repeated once more. Freshly diluted 0.2M NaOH (150μl) was added to each pellet The tube was incubated for 6 minutes at room temperature, Labquaking or tapping the tube frequently. The mixture was spun in a microfuge at setting #10 for 1 minute. The supernatant was removed and retained. The NaOH treatment was repeated and the two supernatants combined. Two hundred μl of ammonium acetate (5M, pH 6.8) was added to the combined supernatants and mixed well. The tubes were spun in the microfuge for 5 minutes at setting #13 to pellet any debris. The supernatant (480 μl) was transferred to a new microcentrifuge tube, leaving 20 μl left in the tube. This pelleting step was repeated once more, with 460 μl being transferred to the top of a centricon-100 tube and 20 μl being left in the microfuge tube.

In the second method, the PCR product was first treated to an optional prespin in a Centricon-100 tube to purify away the amplification primers. Ninety-five to 100 μl PCR product plus 1.9 ml glass distilled $H_2O$ were combined in the top of a Centricon-100 tube and spun for 25 minutes at 3000 rpm in an SA-600 or comparable rotor. The product was then backspun into a retentate tube in a tabletop centrifuge and combined in a 2.0 ml microcentrifuge tube with 100 μl streptavidin (SA) magnetic bead slurry (Promega, catalog #Z5241). The mixture was incubated at room temperature for 30 minutes or more, mixing frequently or rotating on a Labquake apparatus. The mixture was pulse-spun at top speed in the microfuge extremely briefly to remove the liquid and beads from the lid of the tube without spinning the beads to the bottom of the tube. The mixture was gently tritterated with a pipet and the tube was then placed next to a small magnet until the beads collected on the side of the tube. Holding the magnet alongside the tube, the liquid was then pipetted away from the beads without disturbing them. The beads were then washed with 500 μl TE, by shaking gently or Labquaking for 1 minute. The tube was pulse-spun, the sample tritterated and exposed to magnet, and the liquid removed from the beads. The TE wash was repeated once more. Freshly diluted 0.2M NaOH (150 μl) was added to each tube of beads. The tube was incubated for 6 minutes at room temperature, Labquaking or tapping the tube frequently. The tube was pulse-spun, the sample tritterated and exposed to magnet, and the liquid removed from the beads and added to 200 μl ammonium acetate (5M, pH 6.8) already in the top of a centricon-100 tube. The NaOH treatment was repeated and the second supernatant added to the centricon tube as well.

The remainder of the procedure was the same for both methods. The solution was rinsed two times with 2 ml of glass-distilled water by spinning the centricon-100 tube at 3000 rpm for 30 minutes in a Sorvall SS34 or SA600 rotor. An additional spin with another 2 ml of water at 3000 rpm for 45 minutes was done. The Centricon-100 top reservoir was capped and inverted, 20 μl of water were added and the tube was backspun for a short time at 1000 rpm. The retained solution was transferred to a microfuge tube and dried in a Speed Vac evaporator for 1 hour at the medium heat setting. The single-stranded DNA was resuspended in 10 μl $H_2O$. Four to 7.5 μl of the solution was used in a Sequenase sequencing reaction according to manufacturer's instructions (United States Biochemical Corporation, Cleveland, Ohio)

B. Characterization of Oligonucleotide Probes

Oligonucleotide probes for each of the species to be detected were based on two sources of information: (1) the sequence data described in FIG. 2 and (2) data in Genbank. In addition, the nucleotide sequence for *Listeria monocytogenes* was determined experimentally and is identical in the probe region to the sequence published by Collins et al., 1991, *International Journal of Systematic Bacteriology* 41: 240–246. Each of the candidate probes was evaluated using the following steps. First, the nucleotide sequence within the 370 bp region bounded by amplification primers RW01 (SEQ ID No. 27) and DG74 (SEQ ID No. 26) obtained for each species was compared to that of a panel of other species, consisting of species on the meningitis panel (*N. meningitidis*, *S. pneumoniae*, *S. agalactiae*, *H. influenza*, *L. monocytogenes*, and *E. coli*), some closely related species (such as *Pasteurella multocida*, *Neisseria gonorrhoeae*, *N. denitrificans*, and *Kingella indologenes*), and some species considered contaminants (such as *Bacillus substilis*, *B. brevis*). In this manner, regions where differences in the sequence occurred could be found. Most of the differing regions were within "variable regions 8 and 9 " which have been characterized in the scientific literature previously (corresponding approximately to positions 1236–1300 and 1409–1491, respectively, in the *E. coli* 16S rRNA gene). From the regions of sequence variability, candidate 25 base pair probes were chosen.

Second, each oligonucleotide was examined for self-complementary (ability to form base pairs with itself) using a computer program called OLIGO, (National Biosciences, Hamel, Minn.). The position of the oligonucleotide probe was chosen to minimize the formation of secondary structure where it was possible to do so while still maintaining the desired specificity. For example, self-complementarity of more than 6 consecutive bases was avoided.

Third, the candidate probes were compared with the corresponding nucleotide sequence of more phylogenetically diverse species listed in Genbank to find the probes that would not detect other species. In cases where the probe was capable of hybridizing to other species, its location was chosen to minimize hybridization to other pathogenic or contaminant species found in CSF as much as possible. For example, mismatches of a probe to a species which could potentially give a cross-reaction were centered within the probe to minimize the cross reaction.

EXAMPLE 2

Methods for Specificity Testing of Probes

A. PCR Amplification

PCR amplification of bacterial DNA was accomplished as follows.

A standard PCR 2× mix was made containing the following for amplifying a target sequence for bacteria:

| | |
|---|---|
| 10× standard PCR buffer | 10.0 µl |
| 50 mM MgCl$_2$ | 1.0 µl |
| dNTP's (2.5 mM total dNTP's) | 2.5 µl |
| primer RWO1 (SEQ ID No. 27) (50 µM) | 1.0 µl |
| primer DG74 (SEQ ID No. 26) (50 µM) | 1.0 µl |
| H$_2$O | 34.0 µl |
| Taq DNA polymerase (5 U/µl) | 0.5 µl |

The 10× standard PCR buffer contains:

100 mM Tris-HCl, pH 8.3

500 mM KCl 15 mM MgCl 0.1% (w/v) gelatin

Fifty µl of a bacterial DNA sample was mixed together with 50 µl of the PCR 2× mix.

The reaction mixture was placed in a 0.5 ml microfuge tube and the tube was placed in a thermal cycler manufactured by Perkin-Elmer. A two-step PCR cycle was used and the thermocycler was set as follows:

1. Time delay file—5 minutes at 95° C.
2. Thermocycle file—95° C. for 25 seconds 55° C. for 25 seconds for 25 cycles
3. Time delay file—10 minutes at 72° C.

B. Detection of Amplified Products

After the amplification reaction was complete, 5 µl of the 100 µl PCR reaction was mixed with DNA dye buffer (1 µl of 50% sucrose, 10 mM Tris, pH 7.5, 1 mM EDTA, 1.0% SDS, 0.05% bromphenol blue. Alternatively, 0.6 µl of 25% Ficoll, 0.5% bromphenol blue, 0.5% xylene cyanol, 0.5% orange G, 5 mM EDTA, pH 8.0, 0.5% SDS can be used). The sample was loaded onto a 2% Nusieve agarose, 0.5% Seakem agarose, 1×TBE (45 mM Tris-borate, 1 mM EDTA) gel. After running the bromphenol blue or orange G dye front to the bottom of the gel, the gel was stained with ethidium bromide (5 µg/ml), washed in water and photographed under UV light using a Polaroid camera and an orange filter.

The size of the PCR product was approximately 370 bp.

C. Transfer of Amplified DNA to Nylon Membrane

After photography of the gel, the gel was soaked in 0.25N HCl for 10 minutes at room temperature. The gel was then soaked in solution of 0.5N NaOH, 1.5M NaCl for 15 minutes. The gel was then soaked in a solution of 1M Tris, pH 7.5, 1.5M NaCl for 15 minutes. The gel was then rinsed in 20× SSPE.

DNA was then transferred to a nylon membrane (Pall Biodyne) either dry or presoaked in water by one of two ways: (1) vacuum transfer using a Stratagene Stratavac vacuum blotter or (2) capillary transfer by the method of Southern.

After transfer, DNA was fixed to the membrane using UV light in a Stratagene Stratalinker.

D. Radioactive Labeling of Oligonucleotide Probes

The oligonucleotide probes were labeled using T$_4$ polynucleotide kinase in one of the following reaction mixes:

| | Mix 1 | Mix 2 |
|---|---|---|
| $^{32}$P ATP | 10 µl | 6.0 µl |
| 10× kinase buffer | 2.5 µl | 2.5 µl |
| oligonucleotide (10 µM) | 2.0 µl | 1.0 µl |
| H$_2$O | 8.5 µl | 14.5 µl |
| T4 polynucleotide kinase | 2.0 µl | 1.0 µl |

10× kinase buffer contains:

500 mM Tris, pH 8

100 mM MgCl$_2$ 50 mM DTT

The kinase reaction mixture was incubated for 30 minutes at 37° C. 5.6 of 0.25M EDTA and 169.4 µl of H$_2$O were added to stop the reaction. This mixture was loaded onto a 1.0 ml capacity column of Biogel P4 and spun in a tabletop centrifuge for 5 minutes at 2,500 rpm to separate the labeled oligonucleotide from the unincorporated radioactivity. 1 µl of the eluate from the column was counted in a scintillation counter without added scintillation fluid (Cerenkov counting) to obtain an estimate of the level of incorporation of radioactivity. A volume giving approximately 1–2×10$^6$ cpm was used for each blot in the subsequent hybridization.

E. Hybridization of Probes with DNA

The DNA blots were prehybridized in a mixture of 5× SSPE, 0.5% SDS at 60° (1×SSPE=0.18M NaCl, 10 mM NaPO$_4$, pH 7.4, 1 mM EDTA). The labeled oligonucleotide probe was added to 10.0 ml of 5× SSPE, 0.5% SDS and mixed. The solution was added to the plastic bag containing the drained presoaked blot. The blot was incubated for 1 to 18 hours at 60° C.

The blot was removed from the plastic bag and placed in a solution of 2×SSPE, 0.1% SDS and washed for 10 minutes at room temperature. The blot was then washed in a solution of 3M tetramethylammonium chloride (TMACl), 50 mM Tris, pH 8 and 0.2% SDS for 10–20 minutes at room temperature, followed by an additional wash for 10 minutes at 62°–64° C.

The blot was wrapped in Saran wrap and placed in a X-ray film holder with a sheet of Kodak XAR-5 X-ray film with or without an intensifying screen for 1 to 72 hours at −70° C.

EXAMPLE 3

Results of Specificity Testing of Oligontlcleotide Probes

Each of the probes was tested against PCR products from various bacteria listed in FIG. 3. The bacteria selected for testing represent two types of species (1) those of which can be found in cerebrospinal fluid (CSF) either as pathogens or contaminants or (2) those which are closely related to the first type of species. The methods used (for detection of amplified products, transfer of the amplified DNA to nylon membranes, radioactive labeling of oligonucleotide probes and hybridization of probes to the membrane) were as described in Example 2 with temperatures used for the washes in TMACl (tetramethylammonium chloride) ranging from 62° to 66° C. In the hybridization results shown in FIG. 3, the temperature was 66° C. for all probes.

For some of the organisms to be detected, it was unexpectedly found that a number of different probes had to be evaluated before a probe with satisfactory characteristics could be defined. The *Listeria monocytogenes* probe RDR232, (SEQ ID No. 42) 5'-AGGGTAACCTTTATG-GAGCCAGCCG-3', at 62° C. also hybridized to *Bacillus cereus* and slightly to *S. salivarius*; whereas the *L. monocytogenes* probe RDR230 (SEQ ID No. 11) did not hybridize to either of these strains at 62° C., indicating a greater degree of specificity for RDR230 (SEQ ID No. 11). *Streptococcus agalactiae* probes RDR255, (SEQ ID No. 39) 5'-CCTTT-TAGGAGCCAGCCGCCTAAGG-3', and RDR257, (SEQ ID No. 40) 5'-CCTTAGGCGGCTGGCTCCTAAAAGG-3', were found to be unsatisfactory due to poor hybridization signals at 66° C., even though the hybridization signals at 62° C. and 64° C. were satisfactory. In addition, at 64° C., *S. agalactiae* probe RDR255 (SEQ ID No. 39) detected *B. subtilis*, *B. cereus* and *S. salivarius*. *S. agalactiae* probe RDR254, (SEQ ID No. 38) 5'-TAACCTTTAGGAGC-CAGCCGCCTA-3', detected *B. subtilis* in addition to *S. agalactiae* at 66° C. *S. agalactiae* probe RDR306 (SEQ ID No. 20) gave good hybridization signals at 66° C. and did not hybridize to *B. subtilis*, *B. cereus* or *S. salivarius*. Probe RDR324, 5'-CGGTTTCGCTGACCCTTTGTATTGT-3' (SEQ ID No. 41), for the contaminant species *Staphylococcus epidermidis* did not hybridize well at 66° C.; moreover, at lower temperatures (62° C., 64° C.) it hybridized to *S. aureus*, a pathogen. By comparison, *S. epidermidis* probe RDR325 (SEQ ID No. 6) did not hybridize to *S. aureus* at 62° C. or 64° C.

As shown in FIG. 3, each of the probes selected showed a high degree of specificity for the bacterial species tested. In particular, RDR230 (SEQ ID No. 11) (*Listeria monocytogenes*), RDR140 (SEQ ID No. 9) (*E. coli*/enteric bacteria), RDR125 (SEQ ID No. 10) (*Haemophilus influenzae*), RDR328 (SEQ ID No. 15). (*Propionibacterium acnes*) and RDR325 (SEQ ID No. 6) (*Staphylococcus epidermidis*) detected only the intended species among up to 39 different species tested. The *Streptococcus pneumoniae* probe RDR224 (SEQ ID No. 23) hybridized to *S. mitis* and partially to *S. anginosus, S. milleri. S. sanguis*, and *S. intermedius* in addition to *S. pneumoniae*. The cross-reacting species are found in the oral cavity and are not common causes of meningitis. The *Streptococcus agalactiae* probe RDR306 also hybridized to 4 other Streptococci (*S. equi, S.* group G, *S. pyogenes* and *S. dysgalactiae*). Some of these other Streptococci are pathogenic, but are infrequently found in CSF. The *Neisseria meningitidis* probe RDR307 (SEQ ID No. 13) hybridized to *Neisseria sicca* in addition to *N. meningitidis*. *N. sicca* is found in the nasopharynx, saliva and sputum of humans and is not frequently found in CSF. For all of the cross-reacting probes, it is believed that minor and readily determinable modifications confer the required specificity.

EXAMPLE 4

Format II Detection Method

The following demonstrates a preferred embodiment of the invention. A CSF sample suspected of containing nucleic acid from a bacterium is extracted and is amplified with universal bacterial primers RW01 (SEQ ID No. 27) and DG74 (SEQ ID No. 26) as described in Example 2 or 7.

The probes are the same in sequence as those described herein, but are modified to contain 100 to 150 T residues at the 5' end. The probes are fixed to a nylon membrane in a dot blot format by a method similar to that of Saiki et al., 1989. Each dot corresponds to a single probe (one each for the universal bacterial probe, *N. meningitidis* probe, *L. monocytogenes* probe, *E. coli*/enteric bacteria probe, *S. pneumoniae* probe, *S. agalactiae* probe, *H. influenzae* probe, *S. epidermidis* probe, *P. acnes* probe, Bacillus species probe, Corynebacterium species probe, etc.) One strip or set of strips is used for each sample to be tested. The strips are placed in the wells of a plastic tray and 3 to 5 ml of hybridization solution is added (5× SSPE, 0.5% w/v SDS, preheated to 37° C.).

The amplified DNA is denatured by incubation at 95° C. in the heat block of a thermal cycler for 3 to 10 minutes. The tube with the amplified DNA is removed from the heat block and 25–35 µl is immediately removed and added to the well containing the dot blot strip. The tray is incubated at 50° C. to 65° C. in a shaking water bath at 50–90 rpm for 20 to 30 minutes. After hybridization, the solution is aspirated from the well of the tray. The strips are rinsed in 5 ml of wash solution (2.5× SSPE, 0.1% w/v SDS, preheated to 37° C.) at room temperature for 1 to 5 minutes. The wash solution is aspirated and 5 ml more is added. The strips are incubated at 50° to 65° C. for 10 to 15 minutes at 50 rpm. The solution is aspirated and 5 ml of wash solution is added. The strips are incubated for 1 to 5 minutes at room temperature. The wells are aspirated. Five ml of hybridization solution is added and then aspirated.

Three ml of a mixture of 3.3 ml hybridization solution and 27 µl of enzyme conjugate (Amplitype kit [developed and manufactured by Hoffmann-La Roche and marketed by Perkin Elmer] or suitable substitute prepared in a glass flask) per strip is added to each strip and incubated for 30 minutes at room temperature at 50 rpm. Following aspiration wash solution (5 ml) is added and incubated for 5 to 10 minutes at room temperature. Repeat the wash. Citrate solution (0.1M sodium citrate, pH 5.0), 5 ml, is added and incubated at room temperature for 5 minutes. A mixture of 5 ml citrate buffer 5 µl of 3% hydrogen peroxide, and 0.25 ml TMB (Amplitype kit) is added (4 to 5 ml per strip) and incubated for 20 to 30 minutes in the dark to allow color development. To stop color development, the strips are rinsed in distilled water three times. The strips are photographed in visible light against a dark background using Polaroid type 55 or 57 film and an orange filter.

The invention can also be practiced in a microtiter plate format, in which the probes are affixed to the bottom of the wells of a microtiter plate via a thioether linkage to bovine serum albumin (Barone et al., 1991, Abstracts *Am. Soc. Microb.*, page 361).

EXAMPLE 5

Additional Considerations in Design of Probes

Two characteristics are essential for the probes included in the meningitis panel. The first characteristic is the inclusivity of the probe. Probes for a given species preferably detect all strains of the species, including strains of various serotypes that have been classified by their reaction with specific antibodies. For example, the *L. monocytogenes* probe reacts with the following serotypes of *L. monocytogenes*—serotypes ½a, ½b, ½c, 3b, 4b. These serotypes are the ones most commonly found in clinical samples. Most preferably, an *L. monocytogenes* probe reacts with all serotypes of *L. monocytogenes* including ½a, ½b, ½c, 3a, 3b, 3c, 4a, 4b, 4c, 4d, 4e, and 7.

The second characteristic is the exclusivity of the probe. Probes for a given species should not detect other species. Based on DNA sequence comparison, the existing *L. monocytogenes* probe may react with the following Listeria species—*L. innocua, L. welshimeri, L. seeligeri, L. ivanovii*. These other Listeria species are very rarely found in clinical specimens. A preferred probe does not react with any listeria species other than *L. monocytogenes*.

In practice, although it is preferred, it is not essential to achieve the desired inclusivity and exclusivity of a given probe. In these cases, the major considerations in determining the usefulness of a probe in the meningitis assay are: (1) for inclusivity—the probe is able to detect most species found in CSF as pathogens or contaminants and (2) for exclusivity—species that the probe does detect are not commonly found in CSF.

The same considerations discussed above would apply to the other probes on the panel. Hence, the preferred characteristics of the probes are as follows:

*Haemophilus influenzae* probe

Inclusivity—all strains of *H. influenzae* detected

Exclusivity—no species other than *H. influenzae* detected

*S. pneumoniae* probe

Inclusivity—all strains of *S. pneumoniae* detected

Exclusivity—no species other than *S. pneumoniae* detected

The *S. pneumoniae* RDR224 (SEQ ID No. 23) probe gave a weak reaction with the following species: *S. mitis, S. anginosus, S. milleria, S. sanguis*, and *S. intermedius*. Probe RDR462 (SEQ ID No. 24) was designed to improve the specificity of detection. This probe does not cross react with *S. anginosus, S. millei, S. sanguis*, or *S. intermedius*.

*E. coli*/enteric bacteria probe

Inclusivity—detects all strains of all species of enteric bacteria

Exclusivity—no species other than enteric bacteria detected

*Neisseria meningitidis* probe

Inclusivity—detects all serotypes and strains of *N. meningitidis*

Exclusivity—no species other than *N. meningitidis* detected

Probe RDR307 (SEQ ID No. 13) was found to not react with the following serotypes of *N. meningitidis*—serotypes B, C, Y, and W135. To improve the range of detection of this probe, the new probe COR28 (SEQ ID No. 14) was designed and tested. Probe COR28 (SEQ ID No. 14) reacts with the strains of serotypes A, C, B, Y, and W135 of *N. meningitidis* that were tested, but also reacts with the following Neisseria species—*N. gonorrhoeae* and *N. gononhoeae kochii*. Because the latter species is rarely found in CSF, COR28 (SEQ ID No. 14) is considered a suitable probe for detecting bacteria in CSF.

*S. agalactiae* probe

Inclusivity—detects all strains of *S. agalactiae*

Exclusivity—no species other than *S. agalactiae* detected

Corynebacterium species probe

Inclusivity—detects all strains and species of Corynebacterium, including uncharacterized species colonizing human skin Exclusivity—no species other than Corynebacterium detected

*S. epidermidis* and coagulase-negative Staphylococcus probes

Inclusivity—preferably a single probe would detect all strains and species of coagulase-negative Staphylococci Exclusivity—no species other than coagulase-negative Staphylococci detected The *S. epidermidis* probe RDR325 (SEQ ID No. 6) detects *S. epidermidis*, a coagulase-negative Staphylococcus species, but does not detect other coagulase-negative Staphylococci. DNA sequence analysis of the following strains was used to design an improved probe: *S. auricularis, S. saccharolyticus*. The sequence analysis indicated that it was not possible to design a single probe that would detect all three of the coagulase-negative Staphylococcus species. A separate probe, RDR512 (SEQ ID No. 4), was designed which detects *S. auricularis* and *S. saccharolyticus*. Further specificity testing of RDR325 (SEQ ID No. 6) and RDR512 (SEQ ID No. 4) indicated that RDR325 (SEQ ID No. 6) also detects *S. haemolyticus* and RDR512 (SEQ ID No. 4) detects *S. capitis* but neither probe detects other coagulase negative Staphylococcus species such as *S. cohnii, S. hominis, S saprophyticus*, and *S. warneri*.

*S. aureus* probe

Inclusivity—all strains of *S. aureus* detected

Exclusivity—no species other than *S. aureus* detected

Bacillus species probe

Inclusivity—all strains and species of Bacillus detected

Exclusivity—no species other than Bacillus detected

Propionibacterium species probe

Inclusivity—all strains and species of Propionibacterium detected

Exclusivity—no species other than Propionibacterium detected

Probe RDR328 (SEQ ID No. 15) was found to not react with the following Propionibacterium species—*P. avidum, P. granulosum, P. lymphophilum*. Because *P. avidum* and *P. granulosum* are known to colonize human skin, they should be detected by a Propionibacterium species probe. Probe RDR514 (SEQ ID No. 17) was designed and tested as an improvement of RDR328 (SEQ ID No. 15), based on DNA sequence information for these other Propionibacterium species. This probe was found to react with *P. acnes, P. avidum, P. granulosum*, and *P. lymphophilum*.

Changes in the detection scheme necessitate reoptimization of probe sequences and hybridization conditions as described herein. For example, probes that were suitable in a Southern blot format using TMACl (results described in Example 3) were re-evaluated for specificity when used in the reverse dot blot format (method described in Example 4). In order to achieve the required specificity, the *S. pneumoniae*, Bacillus species, and *S. aureus* probes were modified by making them shorter by 2, 4, and 3 bases, respectively. The coagulase-negative Staphylococcus probe was modified by introducing a mismatch in the center. The Corynebacterium species probe was modified by using its reverse complement. A new region was used for the Propionibacterium species probe. The *S. epidermidis* probe was shortened by two bases and the reverse complement was used. A different region was chosen for the modified *S. agalactiae* probe. VP109 (SEQ ID No. 21) was used in the reverse dot-blot format; its reverse complement, KG0001 (SEQ ID No. 22), was used in Southern blot format. These modifications were found to improve the specificity of the probes in reverse dot blot format as demonstrated in FIG. 4.

Additional modifications may improve the performance of probes when using dUTP in the amplification mix. It was found that the signal detected for certain PCR products with certain probes was reduced when dUTP was substituted for TTP in the amplification mix. One possible explanation is that the hybridization efficiency of the U-containing PCR products is reduced relative to that of T-containing PCR products. For the detection of *L. monocytogenes*, a probe selected from the following compositions may give improved performance.

This is the reverse complement of RDR230 (SEQ ID No. 11) SEQ ID No. 32 5'-ACT GAG AAT ACT TTT ATG GGA TTA G-3'

These are located in a different region of the 16S gene and are reverse complements of each other.
SEQ ID No. 33 5'-AGG GTA ACC TTT ATG GAG CCA GCC G-3'
SEQ ID No. 34 5'-CGG CTG GCT CCA TAA AGG TTA CCC T-3' For the detection of *S. agalactiae*, a probe of the following composition may represent an improvement (this is probe KG0001 (SEQ ID No. 22) with 2 bases removed from the 5' end).
SEQ ID No. 35 5'-ATCTCTTAAAGCCAATCTCAGTF-3'

This probe VP109 (SEQ ID No. 21) shortened by 2 bases at the 3' end.
SEQ ID No. 36 5'-AACTGAGATTGGCTTTAAGAGAT-3'

EXAMPLE 6

Preparation of Low-DNA *Taq* Polymerase

To increase sensitivity of the present methods, it may be desirable to use amplification cycle numbers higher than 25 (e.g., 26–40). However, the extreme sensitivity of such a reaction using the universal primers disclosed may lead to artifactual results due to amplification of residual DNA in commercial reagents. For high cycle number the following procedure eliminates DNA contamination in the agent for polymerization.

Equipment Required
  Biorad Econo-pac Q cartridge; Biorad catalog #732-0021
  Sterile disposable 50 mL polypropylene tubes; Corning catalog #25330-50
  HPLC/FPLC flow adaptors; Biorad Catalog #732-0111/ 732-0112.
  General laboratory equipment
  Peristaltic pump (flow rate 0.5–2 mL capability)
Reagents Required
  Formulation buffer: 20 mM Tris, 0.1M KCl, 0.5% NP40, 5% Tween-20, 1 mM DTT, 0.1 mM EDTA, 50% glycerol, pH 8
  Econo-pac Q wash buffer: 200 mM Tris/1M KCl , pH 8.8
  0.5N Acetic acid
  1.0N Sodium hydroxide
  Sterile Glass distilled water
  10% bleach
  70% Ethanol
Procedure
  A. Preparation of Laminar Flow Hood, Peristaltic Pump, and Cartridge Fittings
  1. Wipe down the hood with 10% bleach.
  2. Install the peristaltic pump with tubing and cartridge HPLC/FPLC flow adaptors.
  3. Install the column support stand and clamps into the hood.
  4. Turn on UV lamp for 30 minute to irradiate surfaces.
  5. Rinse pump tubing with 20 mL 70% Ethanol at a flow rate of 1 mL/min.
  6. Rinse tubing with 50 mL sterile glass distilled water at a flow rate of 1 mL/min.
  7. Discard the wash fluid.
  B. Washing the Econo-Pac O Cartridge
  Note: All washes are to be performed using the peristaltic pump at a flow rate not exceeding 2 mL/min. Discard all wash fluid after use. All operations carried out in the hood.
  1. Attach cartridge to the column support stand.
  2. Connect tubing to the cartridge by the flow adaptors.
  3. Wash cartridge with 20 mL sterile GD water.
  4. Wash cartridge with 50 mL 0.5N acetic acid.
  5. Wash cartridge with 50 mL 1.0N sodium hydroxide.
  6. Wash cartridge with 50 mL Econo-pat Q wash buffer.
  7. Wash cartridge with 50 mL Formulation buffer.
  8. Calibrate flow rate to 0.5 mL/min.
  C. Loading and Collecting Ampli Taq® DNA Polymerase
  1. Remove Ampli Taq® DNA polymerase stock from –20° C. freezer. Allow to thaw at room temperature for 30 minutes.
  2. In the hood, add 100 mL of AmpliTaq® DNA polymerase to a sterile, heat treated 250 mL flask.
  3. Replace the stock AmpliTaq® DNA polymerase into the freezer.
  4. Load AmpliTaq® onto the cartridge at a flow rate of 0.5 mL/min.
  5. Collect 5 mL into a tube, then switch to a clean 50 mL tube. Discard the 5 mL aliquot.
  6. Collect 25 mL aliquots of AmpliTaq® DNA polymerase into sterile 50 mL tubes.

EXAMPLE 7

A Preferred Method for Analysis of Clinical Samples

Two modifications of the amplification conditions in Example 2 are preferred when testing clinical samples. First, modifications which greatly reduce the possibility of carry-over contamination are used. The nucleotide dUTP is substituted for TTP in the amplification mix, and uracil-N-glycosylase (UNG) is added to the amplification mix. Under the appropriate conditions of concentration and incubation, these modifications degrade any U-containing PCR product that may contaminate the reaction.

The second modification is to treat the amplification reagents to reduce the level of contaminating bacterial DNA present This allows amplification cycle numbers higher than 25 to be used for increased sensitivity. The 10× *Taq* buffer (100 mM Tris-HCl, pH 8.3, 500 mM KCl) is autoclaved and sterilely dispensed. Eight mM $MgCl_2$ is autoclaved and sterilely dispensed. Water is ultrafiltered and autoclaved. TE buffer (10 mM Tris-HCl, 0.1 mM EDTA, pH 8.0) is autoclaved.

The solution of dNTPs (dATP, dGTP, dCTP, dUTP) is filtered through a Centricon-30 filter (Amicon catalog number 4208). The C-30 filtrate cup and cap are autoclaved and the filter unit is soaked in 10% bleach for 1 hour. The filters are thoroughly rinsed in autoclaved ultrafiltered water. The filters are then spun with 400 μl of autoclaved ultrafiltered water. The dNTP solution is centrifuged through the treated C-30 filter traits once for 30 minutes at 5000 xg in a fixed angle rotor.

The primers at 200 uM concentration are filtered through Millipore M-100 PTHK filters (catalog number UFC3THYK00). The Eppendorf tube part of the filter unit is autoclaved and the filtrate cup is soaked in 10% bleach for 1 hour. The filters are thoroughly rinsed in autoclaved ultrafiltered water. The filters are then spun with 400 μl of autoclaved ultrafiltered water at 5000 xG for 3 minutes in an Eppendorf microfuge. Each primer is successively filtered 4 times, each time through a clean filter for 3 minutes at 5000× g. The primers are diluted 1:250 for a $OD_{260}$ reading. Primer concentration is adjusted using autoclaved TE buffer to 20 um.

The 4× PCR mix is made up as follows:
  400 μl 10X Taq buffer
  40 μl 100 mM dNTP mix or 400 μl of a mixture of equal volumes of 10 mM of each dNTP
  80 μl of 20 uM RW01 (SEQ ID No. 27)
  80 μl of 20 uM DG74 (SEQ ID No. 26)
  20 μl of low-DNA Taq polymerase (5 units/μl)
  380 μl of ultrafiltered water The amplification mix is made up as follows (in order):
  25 μl 4× PCR mix
  25 μl 8 mM $MgCl_2$
  2 drops mineral oil (Sigma #M5904)
  50 μl of DNA sample The amplification conditions in the thermal cycler TC-480 (Perkin Elmer) are:
  50° C., 2 minutes (optional)
  95° C., 1 minute (optional)

Cycling:
  95° C., 1 minute
  55° C., 1 minute for 30 to 35 cycles
  72° C., 7 minutes to overnight Detection is performed as described in Example 4.

Although the foregoing invention has been described in some detail for the purpose of illustration, it will be obvious that changes and modifications may be practiced within the scope of the appended claims by those of ordinary skill in the art.

---

We claim:

1. A method for determining the presence or absence of a bacterium capable of causing meningitis, in a sample suspected of containing said bacterium, said method comprising:

(a) amplifying a target region of a polynucleotide of said bacterium to a detectable level using a pair of oligonucleotide primers consisting of the sequences
5'-AGGAGGTGATCCAACCGCA-3' (SEQ ID NO: 26),
5'-AACTGGAGGAAGGTGGGGGAT-3' (SEQ ID NO: 27), or
the complementary sequences thereto;

(b) mixing the amplified target region of step (a) with an oligonucleotide probe consisting of the sequences selected from the group consisting
5'-CTAATCCCATAAAACTATTCTCAGT-3' (SEQ ID NO: 11),
5'-AAGCCGCGAGGCGGAGCCAATCT-3' (SEQ ID NO: 14),
5'-GGTGTGTACAAGCCCCGGGAACGTA-3' (SEQ ID NO: 17),
5'-TTGCGACTCGTTGTACCAACCATTG-3' (SEQ ID NO: 20),
5'-TATTCACCGCGGCATGCTGAT-3' (SEQ ID NO: 2),
5'-AGTAACCATTTGGAGCTAGCCGT-3' (SEQ ID NO: 3),
5'-CGGCTAGCTCCAAAAGGTTACTCTA-3' (SEQ ID NO: 4),
5'-CGGCTAGCTCTAAAAGGTTACTCTA-3' (SEQ ID NO: 5),
5'-CGACGGCTAGCTCCAAATGGTTACT-3' (SEQ ID NO: 6),
5'-CACATGCTACAAGGGTCGGTACAGT-3' (SEQ ID NO: 7),
5'-CCAACTTTCATGACTTGACGGG-3' (SEQ ID NO: 16),
5'-CCGGTGGAGTAACCTTTTAGGA-3' (SEQ ID NO: 19),
5'-AACTGAGATTGGCTTTAAGAGATTA-3' (SEQ ID NO: 21),
5'-AACTGAGACTGGCTTTAAGAGATTA-3' (SEQ ID NO: 24),
5'-AACTGAGACTGGCTTTAAGAGAT-3' (SEQ ID NO: 25), and
the sequences complementary thereto (c) incubating the amplified target region with said probe under conditions which allow specificity of hybrid duplexes such that said probe should be capable of detecting bacterial species that cause meningicoccal disease and should be capable of excluding non-mengicoccal memingicoccal disease-causing bacterial species commonly found in cerebrospinal fluid; and (d) detecting hybrids formed between said amplified target region and said probe, whereby the presence or absence of the bacterium is determined.

2. The method of claim 1 wherein the target region is amplified by means of polymerase chain reaction.

3. An oligonucleotide probe consisting of a sequence selected from the group consisting of
5'-TATTCACCGCGGCATGCTGAT-3' (SEQ ID NO: 2),
5'-AGTAACCATTTGGACTTAGCCGT-3' (SEQ ID NO: 3),
5'-CGGCTAGCTCCAAAGGTTACTCTA-3' (SEQ ID NO: 4),
5'-CGGCTAGCTCTAAAAGGTTACTCTA-3' (SEQ ID NO: 5),
5'-CGACGGCTAGCTCCAAATGGTTACT-3' (SEQ ID NO: 6),
5'-CACATGCTACAAGGGTCGGTACAGT-3' (SEQ ID NO: 7),
5'-CTAATCCCATAAAACTATTCTCAGT-3' (SEQ ID NO: 11),
5'-AAGCCGCGAGGCGGAGCCAATCT-3' (SEQ ID NO: 14),
5'-CCAACTTTCATGACTTGACGGG-3' (SEQ ID NO: 16),
5'-GGTGTGTACAAGCCCCGGGAACGTA-3' (SEQ ID NO: 17),
5'-CCGGTGGAGTAACCTTTTAGGA-3' (SEQ ID NO: 19),

5'-TTGCGACTCGTTGTACCAACCATTG-3' (SEQ ID NO: 20),

5'-AACTGAGATTGGCTTTAAGAGATTA-3' (SEQ ID NO: 21),

5'-AACTGAGACTGGCTTTAAGAGATTA-3' (SEQ ID NO: 24),

5'-AACTGAGACTGGCFITAAGAGAT-3' (SEQ ID NO: 25), and the complementary sequences thereto.

4. A set of reagents for determining the presence or absence of a bacterium capable of causing meningitis, in a sample suspected of containing said bacterium, comprising a pair of oligonucleotide primers consisting of the sequences

5'-AGGAGGTGATCCAACCGCA-3' (SEQ ID NO: 26),

5'-AACTGGAGGAAGGTGGGGAT-3' (SEQ ID NO: 27), or the complementary sequences thereto; and an oligonucleotide probe selected from the group consisting of the sequences

5'-TATTCACCGCGGCATGCTGAT-3' (SEQ ID NO: 2),

5'-AGTAACCATTTGGACTTAGCCGT-3' (SEQ ID NO: 3),

5'-CGGCTAGCTCCAAAGGTTACTCTA-3' (SEQ ID NO: 4),

5'-CGGCTAGCTCTAAAAGGTTACTCTA-3' (SEQ ID NO: 5),

5'-CGACGGCTAGCTCCAAATGGTTACT-3' (SEQ ID NO: 6),

5'-CACATGCTACAAGGGTCGGTACAGT-3' (SEQ ID NO: 7),

5'-CTAATCCCATAAAACTATTCTCAGT-3' (SEQ ID NO: 11),

5'-AAGCCGCGAGGCGGAGCCAATCT-3' (SEQ ID NO: 14),

5'-CCAACTTTCATGACTTGACGGG-3' (SEQ ID NO: 16),

5'-GGTGTGTACAAGCCCCGGGAACGTA-3' (SEQ ID NO: 17),

5'-CCGGTGGAGTAACCTTTTAGGA-3' (SEQ ID NO: 19),

5'-TTGCGACTCGTTGTACCAACCATTG-3' (SEQ ID NO: 20),

5'-AACTGAGATTGGCTTTAAGAGATTA-3' (SEQ ID NO: 21),

5'-AACTGAGACTGGCTTTAAGAGATTA-3' (SEQ ID NO: 24),

5'-AACTGAGACTGGCFITAAGAGAT-3' (SEQ ID NO: 25), and the complementary sequences thereto:

such that said probe should be capable of detecting bacterial species that cause meningococcal disease and should be capable of excluding non-memingicoccal disease-causing bacterial commonly found in cerebrospinal fluid.

* * * * *

UNITED STATES PATENT AND TRADEMARK OFFICE
CERTIFICATE OF CORRECTION

PATENT NO. : 5,620,847
DATED : April 15, 1997
INVENTOR(S) : Kay S. Greisen, Diane U. Leong It is certified that error appears in the above-identified patent and that said Letters Patent is hereby corrected as shown below:

In claim 1, column 43, line 36, Sequence ID No. 27, delete "5'-AACTGGAGG AGGTGGGGGAT-3'" and insert -- 5'-AACTGGAGGAAGGTGGGGAT-3' --.

In claim 1, column 44, line 36, delete "memingicoccal".

In claim 3, column 44, line 46, Sequence ID No. 3, delete "5'-AGTAACCATTTGG ACTTAGCCGT-3'" and insert -- 5'-AGTAACCATTTGGAGCTAGCCGT-3' --.

In claim 3, column 44, line 48, Sequence ID No. 4, delete "5'-CGGCTAGCT CCAAAGGTTACTCTA-3'" and insert -- 5'-CGGCTAGCTCCAAAAGGTTACT CTA-3' --.

In claim 3, column 45, line 7, Sequence ID No. 25, delete "5'AACT GAGACTGGCFITAAGAGAT-3'" and insert -- 5'-AACTGAGACTGGCTTTAA GAGAT-3' --.

In claim 4, column 45, line 23, Sequence ID No. 3, delete "5'-AGTAACCATTTGG ACTTAGCCGT-3'" and insert -- 5'-AGTAACCATTTGGAGCTAGCCGT-3' --.

In claim 4, column 45, line 25, Sequence ID No. 4, delete "5'-CGGCTAGCT CCAAAGGTTACTCTA-3'" and insert -- 5'-CGGCTAGCTCCAAAAGGTTACT CTA-3' --.

UNITED STATES PATENT AND TRADEMARK OFFICE
CERTIFICATE OF CORRECTION

PATENT NO. : 5,620,847
DATED : April 15, 1997
INVENTOR(S) : Kay S. Greisen, Diane U. Leong It is certified that error appears in the above-identified patent and that said Letters Patent is hereby corrected as shown below:

In claim 4, column 46, line 20, Sequence ID No. 25, delete "5'-AACTGAGACTGG CFITAAGAGAT-3'" and insert -- 5'-AACTGAGACTGGCTTTAAGAGAT-3' --.

In claim 4, column 46, line 25, delete "non-memingicoccal" and insert -- non-meningicoccal--.

In claim 4, column 46, last line, insert -- species -- after the word bacterial.

Signed and Sealed this

Twenty-third Day of September, 1997

*Attest:*

BRUCE LEHMAN

*Attesting Officer*  *Commissioner of Patents and Trademarks*